United States Patent
Dayton et al.

(10) Patent No.: US 9,532,769 B2
(45) Date of Patent: Jan. 3, 2017

(54) SYSTEMS, METHODS, AND COMPUTER READABLE MEDIA FOR HIGH FREQUENCY CONTRAST IMAGING AND IMAGE-GUIDED THERAPEUTICS

(75) Inventors: Paul A. Dayton, Carrboro, NC (US); Ryan Gessner, Carrboro, NC (US); Hyunggyun Lee, Vaughan (CA); Marc Lukacs, Toronto (CA); Francis Stuart Foster, Toronto (CA)

(73) Assignees: THE UNIVERSITY OF NORTH CAROLINA AT CHAPEL HILL, Chapel Hill, NC (US); SUNNYBROOK RESEARCH INSTITUTE, Toronto, Ontario (CA)

(*) Notice: Subject to any disclaimer, the term of this patent is extended or adjusted under 35 U.S.C. 154(b) by 1082 days.

(21) Appl. No.: 13/393,500

(22) PCT Filed: Sep. 7, 2010

(86) PCT No.: PCT/US2010/047988
§ 371 (c)(1),
(2), (4) Date: May 14, 2012

(87) PCT Pub. No.: WO2011/029094
PCT Pub. Date: Mar. 10, 2011

(65) Prior Publication Data
US 2012/0220869 A1 Aug. 30, 2012

Related U.S. Application Data

(60) Provisional application No. 61/240,166, filed on Sep. 4, 2009.

(51) Int. Cl.
*A61B 8/00* (2006.01)
*A61B 8/08* (2006.01)
*A61M 37/00* (2006.01)

(52) U.S. Cl.
CPC .......... *A61B 8/481* (2013.01); *A61M 37/0092* (2013.01)

(58) Field of Classification Search
CPC  A61K 49/223; A61K 49/227; A61K 41/0028; A61N 7/00; A61N 2007/0078; A61B 2019/5276; A61B 5/4839; A61B 8/481
See application file for complete search history.

(56) References Cited

U.S. PATENT DOCUMENTS

| 4,957,656 A | 9/1990 | Cerny et al. |
| 5,469,854 A | 11/1995 | Unger |

(Continued)

FOREIGN PATENT DOCUMENTS

| EP | 1 073 716 B1 | 4/2004 |
| WO | WO-2011/149985 A1 | 12/2011 |

(Continued)

OTHER PUBLICATIONS

Notification of Transmittal of the International Search Report and the Written Opinion of the International Searching Authority, or the Declaration for PCT International Application No. PCT/US2013/063397 (Jan. 16, 2014).

(Continued)

*Primary Examiner* — Elmer Chao
(74) *Attorney, Agent, or Firm* — Jenkins, Wilson, Taylor & Hunt, P.A.

(57) ABSTRACT

Systems, methods, and computer readable media for high-frequency contrast imaging and image-guided therapeutics are disclosed. According to one aspect a method for high frequency contrast imaging and image-guided therapeutics includes: providing ultrasound of a first frequency bandwidth, directed toward the volume to be imaged, the volume containing a carrier having non-linear acoustical properties, wherein the ultrasound of the first frequency bandwidth (Continued)

causes the carrier to generate ultrasound of a second frequency bandwidth that is different from the first frequency bandwidth; receiving, from the volume to be imaged, ultrasound of the second frequency bandwidth; and using the received ultrasound of the second frequency bandwidth to generate an image of the volume to be imaged, wherein the components of the second frequency bandwidth that are detected are of a frequency greater than 20 MHz. According to another aspect, ultrasound at a first frequency bandwidth enables imaging of a target, and ultrasound at a second frequency bandwidth mediates drug or gene delivery to a portion of the target, as guided by the image provided by the first frequency.

24 Claims, 4 Drawing Sheets

(56) References Cited

U.S. PATENT DOCUMENTS

| | | | |
|---|---|---|---|
| 5,558,853 | A | 9/1996 | Quay |
| 5,585,112 | A | 12/1996 | Unger et al. |
| 5,730,955 | A | 3/1998 | Lohrmann |
| 5,740,596 | A | 4/1998 | Corl et al. |
| 5,840,276 | A | 11/1998 | Apfel |
| 5,879,303 | A * | 3/1999 | Averkiou .............. A61B 8/08 600/447 |
| 5,906,580 | A | 5/1999 | Kline-Schoder et al. |
| 6,033,645 | A | 3/2000 | Unger et al. |
| 6,071,495 | A | 6/2000 | Unger et al. |
| 6,312,383 | B1 | 11/2001 | Lizzi et al. |
| 6,409,667 | B1 | 6/2002 | Hossack |
| 6,740,039 | B1 | 5/2004 | Rafter et al. |
| 7,358,226 | B2 | 4/2008 | Dayton et al. |
| 2001/0019710 | A1 | 9/2001 | Berg et al. |
| 2001/0028893 | A1 | 10/2001 | Spears |
| 2002/0099290 | A1 | 7/2002 | Haddad |
| 2003/0165431 | A1 | 9/2003 | Pines et al. |
| 2005/0038423 | A1 | 2/2005 | Makin et al. |
| 2005/0084538 | A1 | 4/2005 | Dayton et al. |
| 2006/0078501 | A1 | 4/2006 | Goertz et al. |
| 2007/0035204 | A1 | 2/2007 | Angelsen et al. |
| 2007/0292495 | A1 | 12/2007 | Ludwig et al. |
| 2008/0182237 | A1 | 7/2008 | Bentwich et al. |
| 2008/0208044 | A1 | 8/2008 | Lecoq et al. |
| 2008/0311046 | A1 | 12/2008 | Kawabata et al. |
| 2009/0076394 | A1 | 3/2009 | Wong et al. |
| 2009/0182237 | A1 | 7/2009 | Angelsen et al. |
| 2009/0317884 | A1 | 12/2009 | Laugharn, Jr. |
| 2010/0224782 | A1 | 9/2010 | Pan et al. |
| 2011/0044903 | A1 | 2/2011 | Borrelli |
| 2013/0336891 | A1 | 12/2013 | Dayton et al. |
| 2015/0252355 | A1 | 9/2015 | Janzen et al. |

FOREIGN PATENT DOCUMENTS

| | | |
|---|---|---|
| WO | WO 2012/048335 A2 | 4/2012 |
| WO | WO 2014/055832 A1 | 4/2014 |
| WO | WO 2015/070186 A1 | 5/2015 |

OTHER PUBLICATIONS

Bekeredjian et al., "Ultrasound-targeted Microbubble Destruction Can Repeatedly Direct Highly Specific Plasmid Expression to the Heart," Circulation—Journal of the American Heart Association, vol. 108, pp. 1022-1026 (2003).
Brennen, "Cavitation and Bubble Dynamics," Oxford University Press (1995).
Sittampalam et al., "High-Throughput Screening: Advances in Assay Technologies," Current Opinion in Chemical Biology, vol. 1(3), pp. 384-391 (1997).
Stieger et al., "Imaging of Angiogenesis Using Cadence Contrast Pulse Sequencing and Targeted Contrast Agents," Contrast Media & Molecular Imaging, vol. 3(1), pp. 9-18 (2008).
Takeuchi et al., "Enhanced Visualization of Intravascular and Left Atrial Appendage Thrombus with the Use of a Thrombus-Targeting Ultrasonographic Contrast Agent (MRX-408A1): In Vivo Experimental Echocardioraphic Studies," Journal of the American Society of Echocardiography, vol. 12, No. 12, pp. 1015-1021 (Dec. 1999).
Tan et al., "Microfluidic Separation of Satellite Droplets as the Basis of a Monodispersed Micron and Submicron Emulsification System," Lab Chip, vol. 5, pp. 1178-1183 (2005).
Tan et al., "Design of Microfludic Channel Geometries for the Control of Droplet Volume, Chemical Concentration, and Sorting," Lab Chip, vol. 4, pp. 292-298 (2004).
Teh et al., "Droplet Microfluidics," Lab Chip, vol. 8, pp. 198-220 (2008).
Tinkov et al., "Microbubbles as Ultrasound Triggered Drug Carriers," Journal of Pharmaceutical Sciences, vol. 98, No. 6, pp. 1935-1961 (2009).
Notification of Transmittal of the International Search Report and the Written Opinion of the International Searching Authority, or the Declaration for International Patent Application No. PCT/US2010/047988 (Mar. 31, 2011).
Restriction and/or Election Requirement for U.S. Appl. No. 13/876,165 (Dec. 1, 2014).
Notification of Transmittal of the International Search Report and the Written Opinion of the International Searching Authority, or the Declaration for International Application No. PCT/US2011/055713 (May 18, 2012).
Alexandridis et al., "Surface Activity of Poly(ethylene oxide)-block-Poly(propylene oxide)-block-Poly(ethylene oxide) Copolymers," Langmuir, vol. 10, pp. 2604-2612 (1994).
Allen et al., "Effect of Coupled Oscillations on Microbubble Behavior," The Journal of the Acoustical Society of America, vol. 14, No. 3, pp. 1678-1690 (Sep. 2003).
Allen, "Liposomes—Opportunities in Drug Delivery," Drugs, vol. 54, Suppl. 4, pp. 8-14 (1997).
Anderson et al., "Ultrasound Molecular Imaging of Tumor Angiogenesis with an Integrin Targeted Microbubble Contrast Agent," Invest Radiol, vol. 46, No. 4, pp. 1-21 (Apr. 2011).
Anderson, "Shotgun DNA Sequencing Using Cloned DNase I-generated Fragments," Nucleic Acids Research, vol. 9, No. 13, pp. 3015-3027 (Jul. 1981).
Aparicio et al., "Chromatin Immunoprecipitation for Determining the Association of Proteins with Specific Genomic Sequences in Vivo," Current Protocols in Cell Biology, Chapter 17, Unit 17.7, pp. 17.7.1-17.7.23 (2004).
Auton et al., "The Force Exerted on a Body in an Inviscid Unsteady Non-Uniform Rotational Flow," J. Fluid Mech., vol. 197, pp. 241-257 (1988).
Behm et al., "Cellular and Molecular Imaging with Targeted Contrast Ultrasound," Ultrasound Quarterly, vol. 22, No. 1, pp. 67-72 (Mar. 2006).
Bernasconi et al., "A Chemogenomic Analysis of the Human Proteome: Application to Enzyme Families," Journal of Biomolecular Screening, vol. 12, No. 7, pp. 972-982 (2007).
Bloch et al., "Targeted Imaging Using Ultrasound Contrast Agents," IEEE Engineering in Medicine and Biology, vol. 23, No. 5, pp. 18-29 (Sep./Oct. 2004).
Böhmer et al., "Preparation of Monodisperse Polymer Particles and Capsules by Ink-Jet Printing," Colloids and Surfaces A: Physicochem. Eng. Aspects, vol. 289, pp. 96-104 (2006).
Borden et al., "A Stimulus-Responsive Contrast Agent for Ultrasound Molecular Imaging," Biomaterials, vol. 29, No. 5, pp. 1-19 (Feb. 2008).
Borden et al., "Ultrasound Radiation Force Modulates Ligand Availability on Targeted Contrast Agents," Molecular Imaging, vol. 5, No. 3, pp. 139-147 (Jul. 2006).
Borden et al., "Influence of Lipid Shell Physicochemical Properties on Ultrasound-Induced Microbubble Destruction," IEEE Transactions on Ultrasonics, Ferroelectrics, and Frequency Control, vol. 52, No. 11, pp. 1992-2002 (Nov. 2005).

(56) References Cited

OTHER PUBLICATIONS

Borden et al., "Surface Phase Behavior and Microstructure of Lipid/PEG-Emulsifier Monolayer-Coated Microbubbles," Colloids and Surfaces B: Biointerfaces, vol. 35, pp. 209-223 (Mar. 2004).
Borden et al., "Dissolution Behavior of Lipid Monolayer-Coated, Air-Filled Microbubbles: Effect of Lipid Hydrophobic Chain Length," Langmuir, vol. 18, pp. 9225-9233 (2002).
Bouakaz et al., "Contrast Superharmonic Imaging: A Feasability Study," Ultrasound in Med. & Biol., vol. 29, No. 4, pp. 547-553 (2003).
Bouakaz et al., "Super Harmonic Imaging: A New Imaging Technique for Improved Contrast Detection," Ultrasound in Med.& Biol., vol. 28, No. 1, pp. 59-68 (2002).
Burger et al., "Sequencing Complete Mitochondrial and Plastid Genomes," Nature Protocols, vol. 2, No. 3, pp. 603-614 (Mar. 22, 2007).
Burns et al., "Microbubble Contrast for Radiological Imaging: 1. Principles," Ultrasound Quarterly, vol. 22, No. 1, pp. 5-13 (Mar. 2006).
Carson et al., "Acoustic Droplet Vaporization," http://www.ultrasound.med.umich.edu/Projects/ADV.html, pp. 1-4 (Downloaded from the Internet Mar. 17, 2015).
Caskey et al., "Direct Observations of Ultrasound Microbubble Contrast Agent Interaction with the Microvessel Wall," The Journal of the Acoustical Society of America, vol. 122, No. 2, pp. 1191-1200 (Aug. 2007).
Chatterjee et al., "A Newtonian Rheological Model for the Interface of Microbubble Contrast Agents," Ultrasound in Med. & Biol.,vol. 29, No. 12, pp. 1749-1757 (Jul. 2003).
Chen et al., "Efficient Gene Delivery to Pancreatic Islets with Ultrasonic Microbubble Destruction Technology," PNAS, vol. 103, No. 22, pp. 8469-8474 (May 30, 2006).
Chen et al., "Multiple Acoustical Matching Layer Design of Ultrasonic Transducer for Medical Application," Jpn. J. Appl. Phys., vol. 41, pp. 6098-6107 (Oct. 2002).
Choi et al., "Spatio-Temporal Analysis of Molecular Delivery Through the Blood-Brain Barrier Using Focused Ultrasound," Physics in Medicine and Biology, vol. 52, pp. 5509-5530 (2007).
Choi et al., "Noninvasive, Transcranial and Localized Opening of the Blood-Brain Barrier Using Focused Ultrasound in Mice," Ultrasound in Medicine and Biology, vol. 33, No. 1, pp. 95-104 (2007).
Chomas et al., "Threshold of Fragmentation for Ultrasonic Contrast Agents," Journal of Biomedical Optics, vol. 6, No. 2, pp. 141-150 (Apr. 2001).
Chomas et al., "Mechanisms of Contrast Agent Destruction," IEEE Transactions Ultrasonics, Ferroelectrics, and Frequency Control, vol. 48, No. 1, pp. 232-248 (Jan. 2001).
Chomas et al., "Optical Observation of Contrast Agent Destruction," Applied Physics Letters, vol. 77, No. 7, pp. 1056-1058 (Aug. 14, 2000).
Chopra et al., "Multifrequency Ultrasound Transducers for Conformal Interstitial Thermal Therapy," IEEE Transactions on Ultrasonics, Ferroelectrics, and Frequency Control, vol. 50, No. 7, pp. 881-889 (Jul. 2003).
Coakley et al., "Ultrasonic Manipulation of Particles and Cells," Bioseparation, vol. 4, pp. 73-83 (1994).
Couture et al., "A Model for Reflectivity Enhancement Due to Surface Bound Submicrometer Particles," Ultrasound in Medicine & Biology, vol. 32, No. 8, pp. 1247-1255 (May 2006).
Couture et al., "Investigating Perfluorohexane Particles with High-frequency Ultrasound," Ultrasound in Medicine & Biology, vol. 32, No. 1, pp. 73-82 (Sep. 2005).
Cronin et al., "Comprehensive Next-Generation Cancer Genome Sequencing in the Era of Targeted Therapy and Personalized Oncology," Biomarkers Med.; 5(3), pp. 293-305 (2011).
Crowder et al., "Sonic Activation of Molecularly-Targeted Nanoparticles Accelerates Transmembrane Lipid Delivery to Cancer Cells Through Contact-mediated Mechanisms: Implications for Enhanced Local Drug Delivery," Ultrasound in Medicine & Biology, vol. 31, pp. 1693-1700 (2005).

Crum, Lawrence A., "Bjerknes Forces on Bubbles in a Stationary Sound Field," The Journal of the Acoustical Society of America, vol. 57, No. 6, Part 1, pp. 1363-1370 (1975).
Crum et al., "The Motion of Bubbles in a Stationary Sound Field," The Journal of the Acoustical Society of America, p. 1411 (1969).
Culp et al., "Successful Microbubble Sonothrombolysis Without Tissue Plasminogen Activator in a Rabbit Model of Acute Ischemic Stroke," Stroke, vol. 42, No. 8, pp. 1-15 (Aug. 2011).
Dayton et al., "Application of Ultrasound to Selectively Localize Nanodroplets for Targeted Imaging and Therapy," Molecular Imaging, vol. 5, No. 3, pp. 1-32 (Jul. 2006).
Dayton et al., "Ultrasound-Mediated Therapies Using Oil and Perfluorocarbon-Filled Nanodroplets," Drug Development Research, vol. 67, pp. 42-46 (2006).
Dayton et al., "Ultrasonic Analysis of Peptide- and Antibody-Targeted Microbubble Contrast Agents for Molecular Imaging of $\alpha v \beta 3$-expressing Cells," Molecular Imaging, vol. 3, No. 2, pp. 1-18 (Apr. 2004).
Dayton et al., "Targeted Imaging Using Ultrasound," Journal of Magnetic Resonance Imaging, vol. 16, pp. 362-377 (2002).
Dayton et al., "The Magnitude of Radiation Force on Ultrasound Contrast Agents," The Journal of the Acoustical Society of America, vol. 112, No. 5, Part 1, pp. 2183-2192 (2002).
Dayton et al., "Optical and Acoustical Dynamics of Microbubble Contrast Agents Inside Neutrophils," Biophysical Journal, vol. 80, pp. 1547-1556 (Mar. 2001).
Dayton et al., "Acoustic Radiation Force in Vivo: A Mechanism to Assist Targeting of Microbubbles," Ultrasound in Med. and Biol. vol. 25, No. 8, pp. 1195-1201 (1999).
Dayton et al., "Optical and Acoustical Observations of the Effects of Ultrasound on Contrast Agents," IEEE Transactions on Ultrasonics, Ferroelectrics, and Frequency Control,vol. 46, No. 1, pp. 220-232 (Jan. 1999).
Dayton et al., "A Preliminary Evaluation of the Effects of Primary and Secondary Radiation Forces on Acoustic Contrast Agents," IEEE Transactions on Ultrasonics, Ferroelectrics, and Frequency Control, vol. 44, No. 6, pp. 1264-127 (Nov. 1997).
Dayton et al., "Action of Microbubbles When Insonified: Experimental Evidence," IEEE Ultrasonics Symposium, vol. 2, pp. 1131-1134 (1996).
Deininger, "Random Subcloning of Sonicated DNA: Application to Shotgun DNA Sequence Analysis," Analytical Biochemistry, vol. 129(1), pp. 216-223 (1983).
Deng et al., "Ultrasound-Induced Cell Membrane Porosity," Ultrasound in Medicine & Biology, vol. 30, No. 4, pp. 519-526 (2004).
Desilets et al., "Design of Efficient Broad-Band Piezoelectric Transducers," IEEE Transactions on Sonics and Ultrasonics, vol. SU-25, No. 3, pp. 115-125 (May 1978).
Doinikov et al., "Modeling of Nonlinear Viscous Stress in Encapsulating Shells of Lipid-Coated Contrast Agent Microbubbles," Ultrasonics, vol. 49, No. 2, pp. 1-17 (Feb. 2009).
Doinikov et al., "Resonance Frequencies of Lipid-Shelled Microbubbles in the Regime of Nonlinear Oscillations," Ultrasonics, vol. 49, No. 2, pp. 1-16 (Feb. 2009).
Doinikov et al., "Modeling of the Acoustic Response From Contrast Agent Microbubbles Near a Rigid Wall," Ultrasonics, vol. 49, No. 2, pp. 1-17 (Feb. 2009).
Doinikov et al., "Maxwell Rheological Model for Lipid-Shelled Ultrasound Microbubble Contrast Agents," The Journal of the Acoustical Society of America, vol. 121, No. 6, pp. 1-26 (Jun. 2007).
Doinikov et al., "Spatio-temporal Dynamics of an Encapsulated Gas Bubble in an Ultrasound Field," The Journal of the Acoustical Society of America, vol. 120, No. 2, pp. 1-25 (Aug. 2006).
Dromi et al., "Pulsed-High Intensity Focused Ultrasound and Low Temperature Sensitive Liposomes for Enhanced Targeted Drug Delivery and Antitumor Effect," Clinical Cancer Research, vol. 13, pp. 2722-2727 (2007).
Ellegala et al., "Imaging Tumor Angiogenesis with Contrast Ultrasound and Microbubbles Targeted to $\alpha v \beta 3$," Circulation, Journal of the American Heart Association, vol. 108 pp. 336-341 (2003).
Evans et al., "Physical Properties of Phase-Change Emulsions," Langmuir, vol. 22, pp. 9538-9545 (Sep. 2006).

(56) References Cited

OTHER PUBLICATIONS

Fabiilli et al., "Delivery of Chlorambucil Using an Acoustically Triggered Perfluoropentane Emulsion," Ultrasound in Medicine and Biology, vol. 36, No. 8, pp. 1-25 (Aug. 2010).
Fabiilli et al., "Delivery of Water-Soluble Drugs Using Acoustically Triggered Perfluorocarbon Double Emulsions," Pharm. Res., vol. 27, No. 12, pp. 1-25 (Dec. 2010).
Fabiilli et al., "The Role of Inertial Cavitation in Acoustic Droplet Vaporization," IEEE Transactions on Ultrasonics, Ferroelectrics, and Frequency Control, vol. 56, No. 5, pp. 1-24 (May 2009).
Farook et al., "Controlling Size and Size Distribution of Electrohydrodynamically Prepared Microbubbles," Bubble Science, Engineering and Technology, vol. 1, No. 1/2, pp. 53-57 (2009).
Farook et al., "Preparation of Suspensions of Phospholipid-coated Microbubbles by Coaxial Electrohydrodynamic Atomization," The Journal of the Royal Society Interface, vol. 6, (32), pp. 271-277 (Jul. 2008).
Ferrara, "Driving Delivery Vehicles with Ultrasound," Advanced Drug Delivery Reviews, vol. 60, No. 10, pp. 1-9 (Jun. 30, 2008).
Ferrara et al., "Ultrasound Microbubble Contrast Agents: Fundamentals and Application to Gene and Drug Delivery," The Annual Review of Biomedical Engineering, vol. 9, pp. 415-447 (2007).
Ferretti et al., "Tumor Interstitial Fluid Pressure as an Early-Response Marker for Anticancer Therapeutics," Neoplasia, vol. 11, No. 9, pp. 874-81 (Sep. 2009).
Feshitan et al., "Microbubble Size Isolation by Differential Centrifugation," Journal of Colloid and Interface Science, 329, pp. 316-324 (2009).
Ganan-Calvo et al., "Perfectly Monodisperse Microbubbling by Capillary Flow Focusing," Physical Review Letters, vol. 87, No. 27, pp. 274501-1-274501-4 (2001).
Gao et al., "Drug-Loaded Nano/Microbubbles for Combining Ultrasonography and Targeted Chemotherapy," Ultrasonics, vol. 48, No. 4, pp. 1-24 (Aug. 2008).
Garstecki et al., "Formation of Bubbles and Droplets in Microfluidic Systems," Bulletin of the Polish Academy of Sciences, vol. 53, No. 4, pp. 361-372 (2005).
Gessner et al., "High-Resolution, High-Contrast Ultrasound Imaging Using a Prototype Dual-Frequency Transducer: In Vitro and In Vivo Studies," IEEE Transactions on Ultrasonics, Ferroelectrics, and Frequency Control, vol. 57, No. 8, pp. 1772-1781 (Aug. 2010).
Gessner et al., "Advances in Molecular Imaging with Ultrasound," Mol Imaging, vol. 9, No. 3, pp. 1-21 (Jun. 2010).
Gessner et al., "Radiation Force-Enhanced Targeted Imaging and Near Real-time Molecular Imaging Using a Dual-Frequency High-Resolution Transducer: In-vitro and In-vivo Results," Proceedings of the 2009 IEEE Ultrasonics Symposium, In Press, pp. 1-4, (2009).
Gessner et al., "Radiation Force-Enhanced Targeted Imaging Using a Dual-Frequency High Resolution Transducer," Abstract Submitted for Peer Review (Publication Date Unknown).
Gessner et al., "High-Resolution In-Vivo Ultraharmonic Contrast Imaging using a Dual-Frequency Transducer," Abstract Submitter for Peer Review (Publication Date Unknown).
Giesecke et al., "Ultrasound-Mediated Cavitation Thresholds of Liquid Perfluorocarbon Droplets in Vitro," Ultrasound in Medicine & Biology, vol. 29, No. 9, pp. 1359-1365 (2003).
Gingrich et al., "Partial CviJI Digestion as an Alternative Approach to Generate Cosmid Sublibraries for Large-Scale Sequencing Projects," Biotechniques, vol. 21 (1), pp. 99-104 (1996).
Giresi et al., "Isolation of Active Regulatory Elements from Eukaryotic Chromatin Using FAIRE (Formaldehyde Assisted Isolation of Regulatory Elements)," Methods, vol. 48, No. 3, pp. 1-13 (Jul. 2009).
Goll, "Design of Broad-Band Fluid-Loaded Ultrasonic Transducers," IEEE Transactions on Sonics and Ultrasonics, vol. SU-26, No. 6, pp. 385-393 (Nov. 1979).
Groschl, "Ultrasonic Separation of Suspended Particles—Part I: Fundamentals," Acustica, vol. 84, pp. 432-447 (1998).

Haworth et al., "Towards Aberration Correction of Transcranial Ultrasound Using Acoustic Droplet Vaporization," Ultrasound Med Biol, vol. 34, No. 3, pp. 1-24 (Mar. 2008).
Hen en, "Shearing DNA for Genomic Library Construction," Trends in Biochemical Sciences, vol. 22, pp. 273-274 (1997).
Hettiarachchi et al., "Controllable Microfluidic Synthesis of Multiphase Drug-Carrying Liposheres for Site-Targeted Therapy," Biotechnology Progress, vol. 25, No. 4, pp. 1-17 (2009).
Hettiarachchi et al., "On-chip Generation of Microbubbles as a Practical Technology for Manufacturing Contrast Agents for Ultrasonic Imaging," Lab Chip., vol. 7, No. 4, pp. 1-14 (Apr. 2007).
Hitchcock et al., "Ultrasound-Assisted Thrombolysis for Stroke Therapy: Better Thrombus Break-up with Bubbles," Stroke, vol. 41, pp. 1-8 (Oct. 2010).
Hobbs et al., "Regulation of Transport Pathways in Tumor Vessels: Role of Tumor Type and Microenvironment," Proceedings of the National Academy of Sciences, vol. 95, No. 8, pp. 4607-4612 (Apr. 1998).
Hoff et al., "Oscillations of Polymeric Microbubbles: Effect of the Encapsulating Shell," The Journal of the Acoustical Society of America, vol. 107, No. 4, pp. 2272-2280 (2000).
Hoffman et al. "Genome-Wide Identification of DNA-Protein Interactions Using Chromatin Immunoprecipitation Coupled with Flow Cell Sequencing," Journal of Endocrinology, vol. 201(1), pp. 1-13 (2009).
Hoheisel et al., "Control of Partial Digestion Combining the Enzymes dam Methylase and Mbol," Nucleic Acids Research, vol. 17, No. 23, pp. 9571-9582 (1989).
Hopp et al., "Factory Physics, Foundations of Manufacturing Management," Second Edition, Chapter 7, pp. 213-227 (2008).
Huh et al., "A Gravity-Driven Microfluidic Particle Sorting Device with Hydrodynamic Separation Amplification," Analytical Chemistry, vol. 79, pp. 1-14 (Feb. 2007).
Hynynen et al., "Local and Reversible Blood-Brain Barrier Disruption by Noninvasive Focused Ultrasound at Frequencies Suitable for Trans-skull Sonications," NeuroImage, vol. 24, pp. 12-20 (2005).
Iyer et al., "Exploiting the Enhanced Permeability and Retention Effect for Tumor Targeting," Drug Discovery Today, vol. 11, No. 17/18, pp. 812-818 (2006).
Janzen et al., "Epigenetics: Tools and Technologies," Drug Discov Today Technol., vol. 7, No. 1, pp. 1-13 (2010).
Janzen et al., "High Throughput Screening. Methods and Protocols, Second Edition," (2009).
Janzen et al., "Review: Advances in Improving the Quality and Flexibility of Compound Management," Journal of Biomolecular Screening, vol. 14, No. 5, pp. 444-451 (2009).
Janzen, "High Throughput Screening: Methods and Protocols," (2002).
Jayaweera et al., "In Vivo Myocardial Kinetics of Air-Filled Albumin Microbubbles During Myocardial Contrast Echocardiography. Comparison with Radiolabeled Red Blood Cells," Circulation Research—The Journal of the American Heart Association, vol. 74, No. 6, pp. 1157-1165 (1994).
Jones et al., "Prospective Thermal Dosimetry: The Key to Hyperthermia's Future," International Journal of Hyperthermia, vol. 22, No. 3, pp. 247-253 (May 2006).
Kawabata et al., "Nanoparticles with Multiple Perfluorocarbons for Controllable Ultrasonically Induced Phase Shifting," Japanese Journal of Applied Physics, vol. 44, No. 6B, pp. 4548-4552 (2005).
Kaya et al., "Acoustic Responses of Monodisperse Lipid Encapsulated Microbubble Contrast Agents Produced by Flow Focusing," Bubble Science, Engineering and Technolology, vol. 2, No. 2, pp. 33-40 (Dec. 2010).
Kaya et al., "Changes in Lipid-Encapsulated Microbubble Population During Continuous Infusion and Methods to Maintain Consistency," Ultrasound in Medicine & Biology, vol. 35, No. 10, pp. 1-16 (Oct. 2009).
Klibanov, "Microbubble Contrast Agents—Targeted Ultrasound Imaging and Ultrasound-Assisted Drug-Delivery Applications," Investigative Radiology, vol. 41, No. 3, pp. 354-362 (2006).
Klibanov et al., "Targeting and Ultrasound Imaging of Microbubble-based Contrast Agents," Magnetic Resonance Materials in Physics, Biology, and Medicine, vol. 8, pp. 177-184 (1999).

(56) References Cited

OTHER PUBLICATIONS

Klibanov et al., "Targeting of Ultrasound Contrast Material. An in vitro Feasibility Study," Acta Radiologica, Supplement 412, pp. 113-120 (1997).
Knierim et al., "Systematic Comparison of Three Methods for Fragmentation of Long-range PCR Products for Next Generation Sequencing," PLoS ONE, vol. 6, Issue 11, e28240, pp. 1-6 (Nov. 2011).
Kripfgans et al., "Acoustic Droplet Vaporization for Temporal and Spatial Control of Tissue Occlusion: A Kidney Study," IEEE Transactions on Ultrasonics, Ferroelectrics, and Frequency Control, vol. 52, No. 7, pp. 1101-1110 (2005).
Kripfgans et al., "On the Acoustic Vaporization of Micrometer-Sized Droplets," The Journal of the Acoustical Society of America, vol. 116, No. 1, pp. 272-281 (2004).
Kripfgans et al., "In Vivo Droplet Vaporization for Occlusion Therapy and Phase Aberration Correction," IEEE Transactions on Ultrasonics, Ferroelectrics, and Frequency Control, vol. 49, pp. 726-738 (2002).
Kripfgans et al., "Acoustic Droplet Vaporization for Therapeutic and Diagnostic Applications," Ultrasound in Med. & Biol., vol. 26, No. 7, pp. 1177-1189 (2000).
Krishnan et al., "Inertial lift on a Moving Sphere in Contact with a Plane Wall in a Shear Flow," Phys. Fluids, vol. 7, No. 11, pp. 2538-2545 (1995).
Kruse et al., "Spatial and Temporal-Controlled Tissue Heating on a Modified Clinical Ultrasound Scanner for Generating Mild Hyperthermia in Tumors," IEEE Transactions on Biomedical Engineering, vol. 57, No. 1, pp. 155-166 (Jan. 2010).
Kruse et al., "A New Imaging Strategy Using Wideband Transient Response of Ultrasound Contrast Agents," IEEE Transactions on Ultrasonics, Ferroelectrics and Frequency Control, vol. 52, No. 8, pp. 1-22 (Aug. 2005).
Kwan et al., "Microbubble Dissolution in a Multigas Environment," Langmuir, vol. 26, No. 9,, pp. 6542-6548 (2010).
Lamberti et al., "A New Approach for the Design of Ultrasono-Therapy Transducers," IEEE Transactions on Ultrasonics, Ferroelectrics, and Frequency Control, vol. 44, No. 1, pp. 77-84 (Jan. 1997).
Landmark et al., "Pharmacokinetics of Perfluorobutane Following Intravenous Bolus Injection and Continuous Infusion of Sonazoid™ in Healthy Volunteers and in Patients with Reduced Pulmonary Diffusing Capacity," Ultrasound in Med. & Biol., vol. 34, No. 3, pp. 494-501 (2008).
Lanza et al., "Targeted Ultrasonic Contrast Agents for Molecular Imaging and Therapy," Current Problems in Cardiology, pp. 625-653 (Dec. 2003).
Lanza et al., "High-Frequency Ultrasonic Detection of Thrombi with a Targeted Contrast System," Ultrasound in Med. & Biol., vol. 23, No. 6, pp. 863-870 (1997).
Lanza et al., "A Novel Site-Targeted Ultrasonic Contrast Agent with Broad Biomedical Application," Circulation, vol. 94. pp. 1-9 (1996).
Lee et al., "Oscillatory Vaporization and Acoustic Response of Droplet at High Pressure," International Communications in Heat and Mass Transfer, vol. 35, No. 10, pp. 1302-1306 (2008).
Leong-Poi et al., "Noninvasive Assessment of Angiogenesis by Ultrasound and Microbubbles Targeted to αv-Integrins," Circulation—Journal of the American Heart Association, vol. 107, pp. 455-460 (2003).
Lindner, "Contrast Ultrasound Molecular Imaging of Inflammation in Cardiovascular Disease," Cardiovascular Research, vol. 84, pp. 182-189 (2009).
Lindner, "Microbubbles in Medical Imaging: Current Applications and Future Directions," Nature Reviews—Drug Discovery, vol. 3, pp. 527-532 (Jun. 2004).
Lindner, "Evolving Applications for Contrast Ultrasound," The American Journal of Cardiology, vol. 90, No. 10A, pp. 72J-80J (2002).

Lindner et al., "Delivery of Drugs with Ultrasound," Echocardiography, vol. 18, No. 4, pp. 329-337 (May 2001).
Lindner et al., "Assessment of Resting Perfusion with Myocardial Contrast Echocardiography: Theoretical and Practical Considerations," The American Heart Journal, vol. 139, No. 2, Part 1, pp. 231-240 (2000).
Lindner et al., "Noninvasive Ultrasound Imaging of Inflammation Using Microbubbles Targeted to Activated Leukocytes," Circulation—Journal of the American Heart Association, vol. 102, No. 22, pp. 2745-2750 (2000).
Linker et al., "In Vivo Molecular Imaging of Adhesion Molecules in Experimental Autoimmune Encephalomyelitis (EAE)," Journal of Autoimmunity, vol. 25, pp. 199-205 (2005).
Lo et al., "Acoustic Droplet Vaporization Threshold: Effects of Pulse Duration and Contrast Agent," IEEE Transactions on Ultrasonics, Ferroelectrics, and Frequency Control, vol. 54, No. 5, pp. 933-946 (2007).
Lo et al., "Spatial Control of Gas Bubbles and Their Effects on Acoustic Fields," Ultrasound Med Biol., vol. 32, No. 1, pp. 95-106 (2006).
Lockwood et al., "Modeling and Optimization of High-Frequency Ultrasound Transducers," IEEE Transactions on Ultrasonics, Ferroelectrics, and Frequency Control, vol. 41, No. 2, pp. 225-230 (Mar. 1994).
Lum et al., "Ultrasound Radiation Force Enables Targeted Deposition of Model Drug Carriers Loaded on Microbubbles," Journal of Controlled Release, vol. 111, No. 1-2, pp. 1-15 (Mar. 2006).
Macedo et al., "Acoustic Effects on Gas Bubbles in the Flows of Viscous Fluids and Whole Blood," The Journal of the Acoustical Society of America, vol. 53, No. 5, pp. 1327-1335 (1973).
Marmottant et al., "A Model for Large Amplitude Oscillations of Coated Bubbles Accounting for Buckling and Rupture," The Journal of the Acoustical Society of America, vol. 118, No. 6, pp. 3499-3505 (2005).
Marsh et al., "Molecular Imaging with Targeted Perfluorocarbon Nanoparticles: Quantification of the Concentration Dependence of Contrast Enhancement for Binding to Sparse Cellular Epitopes," Ultrasound Med Biol., vol. 33, No. 6, pp. 1-16 (Jun. 2007).
Martz et al., "Precision Manufacture of Phase-Change Perflurocarbon Droplets Using Microfluidics," Ultrasound Med Biol., vol. 37, No. 11, pp. 1-13 (Nov. 2011).
Matsuura et al., "Nanoparticle-Loaded Perfluorocarbon Droplets for Imaging and Therapy," IEEE International Ultrasonics Symposium (IUS), pp. 5-8 (2009).
Mattrey, "The Potential Role of Perfluorochemicals (PFCs) in Diagnostic Imaging," Artificial Cells, Blood Substitutes, and Immobilization Biotechnology, vol. 22, No. 2, pp. 295-313 (1994).
McKeighen, "Design Guidelines for Medical Ultrasonic Arrays," SPIE, vol. 3341, pp. 1-18 (1998).
Meairs et al., "Microbubbles for Thrombolysis of Acute Ischemic Stroke," Cerebrovascular Diseases, vol. 27, pp. 55-65 (Apr. 16, 2009).
Meyer et al., "Freestream Nuclei and Traveling-Bubble Cavitation," Transactions of the ASME, vol. 114, pp. 672-679 (Dec. 1992).
Meyerson et al., "Advances in Understanding Cancer Genomes Through Second-Generation Sequencing," Nature Reviews, Genetics, vol. 11, pp. 685-696 (Oct. 2010).
Miller et al., "Bioeffects Considerations for Diagnostic Ultrasound Contrast Agents," J Ultrasound Med, vol. 27, pp. 611-632 (2008).
Miller et al., "Lysis and Sonoporation of Epidermoid and Phagocytic Monolayer Cells by Diagnostic Ultrasound Activation of Contrast Agent Gas Bodies," Ultrasound in Medicine and Biology, vol. 27, No. 8, pp. 1107-1113 (2001).
Miller et al., "Sonoporation of Monolayer Cells by Diagnostic Ultrasound Activation of Contrast-Agent Gas Bodies," Ultrasound in Medicine and Biology, vol. 26, No. 4, pp. 661-667 (2000).
Miller et al., "Cavitation Nucleation Agents for Nonthermal Ultrasound Therapy," Journal of the Acoustical Society of America, vol. 107, No. 6, pp. 3480-3486 (Jun. 2000).
Miller et al., "Sonoporation of Cultured Cells in the Rotating Tube Exposure System," Ultrasound in Medicine and Biology, vol. 25, No. 1, pp. 143-449 (1999).

(56) References Cited

OTHER PUBLICATIONS

Mitragotri, "Healing Sound: The Use of Ultrasound in Drug Delivery and Other Theraputic Applications," Nature Reviews, Drug Discovery, vol. 4, pp. 255-260 (Mar. 2005).
Morgan, "Experimental and Theoretical Evaluation of Ultrasonic Contrast Agent Behavior," Dissertation, University of Virginia, (Jan. 2001).
Morgan et al., "Experimental and Theoretical Evaluation of Microbubble Behavior: Effect of Transmitted Phase and Bubble Size," IEEE Transactions on Ultrasonics, Ferroelectrics, and Frequency Control, vol. 47, No. 6, pp. 1494-1509 (Nov. 2000).
Morgan et al., "Experimental and Theoretical Analysis of Individual Contrast Agent Behavior," IEEE Ultrasonics Symposium, vol. 2, pp. 1685-1688 (1999).
Morgan et al., "Changes in the Echoes from Ultrasonic Contrast Agents with Imaging Parameters," IEEE Transactions on Ultlrasonics, Ferroelectrics, and Frequency Control, vol. 45, No. 6, pp. 1537-1548 (Nov. 1998).
Mullin et al., "Effect of Anesthesia Carrier Gas on In-Vivo Circulation Times of Ultrasound Microbubble Contrast Agents in Rats," Contrast Media Mol Imaging, vol. 6, No. 3, pp. 1-14 (2011).
Mulvagh et al., "Contrast Echocardiography: Current and Future Applications," Journal of the American Society of Echocardiography, vol. 13, No. 4, pp. 331-342 (Apr. 2000).
Nyborg, "Solutions of the Bio-Heat Transfer Equation," Physics in Medicine and Biology, vol. 33, No. 7, pp. 785-792 (1988).
Oakley, "Calculation of Ultrasonic Transducer Signal-to-Noise Rations Using the KLM Model," IEEE Transactions on Ultrasonics, Ferroelectrics, and Frequency Control, vol. 44, No. 5, pp. 1018-1026 (Sep. 1997).
Oefner et al., "Efficient Random Subcloning of DNA Sheared in a Recirculating Point-Sink Flow System," Nucleic Acids Research, vol. 24, No. 20, pp. 3879-3886 (1996).
Osoegawa et al., "A Bacterial Artificial Chromosome Library for Sequencing the Complete Human Genome," Genome Research, vol. 11, No. 3, pp. 483-496 (2001).
Pan et al., "Study of Sonoporation Dynamics Affected by Ultrasound Duty Cycle," Ultrasound in Medicine and Biology, vol. 31, No. 6, pp. 849-856 (2005).
Pan et al., "Sonoporation of Cells for Drug and Gene Delivery," Conf Proc IEEE Eng Med Biol Soc, vol. 5, pp. 3531-3534 (2004).
Pancholi et al., "Novel Methods for Preparing Phospholipid Coated Microbubbles," Eur. Blophys. J., vol. 37, pp. 515-520 (2008).
Pancholi et al., "Generation of Microbubbles for Diagnostic and Therapeutic Applications Using a Novel Device," Journal of Drug Targeting, vol. 16, No. 6, pp. 494-501 (Jul. 2008).
Park et al., "Unsteady Forces on Spherical Bubbles," Experimnets in Fluids, vol. 19, pp. 167-172 (1995).
Patil et al., "Particle Diameter Influences Adhesion Under Flow," Biophysical Journal, vol. 80, pp. 1733-1743 (Apr. 2001).
Pitt et al., "Ultrasonic Drug Delivery—A General Review," Expert Opinion on Drug Delivery, vol. 1, pp. 1-32 (Nov. 2004).
Plesset et al., "Bubble Dynamics and Cavitation," Annu. Rev. Fluid Mech., vol. 9, pp. 145-185 (1977).
Popa-Burke et al., "Streamlined System for Purifying and Quantifying a Diverse Library of Compounds and the Effect of Compound Concentration Measurements on the Accurate Interpretation of Biological Assay Results," Analytical Chemistry, vol. 76, No. 24, pp. 7278-7287 (Dec. 15, 2004).
Price et al., "Delivery of Colloidal Particles and Red Blood Cells to Tissue Through Microvessel Ruptures Created by Targeted Microbubble Destruction with Ultrasound," Journal of the American Heart Association, vol. 98, pp. 1264-1267 (Sep. 29, 1998).
Prosperetti, "Bubble Phenomena in Sound Fields: Part Two," Ultrasonics, vol. 22, pp. 115-124 (May 1984).
Qamar et al., "Dynamics of Acoustic Droplet Vaporization in Gas Embolotherapy," Applied Physics Letters, vol. 96, pp. 143702-1-143702-3 (2010).
Rapoport et al., "Cavitation Properties of Block Copolymer Stabilized Phase-Shift Nanoemulsions Used as Drug Carriers," Ultrasound Med Biol, vol. 36, No. 3, pp. 1-21 (Mar. 2010).
Rapoport et al., "Controlled and Targeted Tumor Chemotherapy by Ultrasound-activated Nanoemulsions/Microbubbles," J Control Release, vol. 138, No. 3, pp. 1-25 (Sep. 15, 2009).
Rapoport et al., "Microbubble Generation in Phase-Shift Nanoemulsions Used as Anticancer Drug Carriers," Bubble Sci Eng Technol, vol. 1, pp. 1-21 (2009).
Rapoport et al., "Multifunctional Nanoparticles for Combining Ultrasonic Tumor Imaging and Targeted Chemotherapy," J Natl Cancer Inst, vol. 99, pp. 1095-1106 (2007).
Reddy et al., "Coupled Dynamics of Translation and Collapse of Acoustically Driven Microbubbles," J. Acoust. Soc. Am., vol. 112, No. 4, pp. 1346-1352 (Oct. 2002).
Reinhardt et al., "Ultrasound Derived Imaging and Quantification of Cell Adhesion Molecules in Experimental Autoimmune Encephalomyelitis (EAE) by Sensitive Particle Acoustic Quantification (SPAQ)," NeuroImage, vol. 27, pp. 267-278 (2005).
Roe, "Shotgun Library Construction for DNA Sequencing," Methods in Molecular Biology, vol. 255, pp. 171-187 (2004).
Rychak et al., "Enhanced Targeting of Ultrasound Contrast Agents Using Acoustic Radiation Force," Ultrasound in Medicine and Biology, vol. 33, No. 7, pp. 1132-1139 (Jul. 2007).
Rychak et al., "Acoustic Radiation Force Enhances Targeted Delivery of Ultrasound Contrast Microbubbles: In Vitro Verification," IEEE Transactions on Ultrasonics, Ferroelectrices, and Frequency Control, vol. 52, No. 3, pp. 421-433 (Mar. 2005).
Rychak et al., "Deformable Gas-Filled Microbubbles Targeted to P-Selectin," Journal of Controlled Release, vol. 114, pp. 288-299 (2006).
Sboros et al., "The Assessment of Microvascular Flow and Tissue Perfusion Using Ultrasound Imaging," Proceedings of the Institution of Mechanical Engineers, Part H: Journal of Engineerying in Medicince, vol. 224, pp. 273-290 (2010).
Sboros, "Response of Contrast Agents to Ultrasound," Advanced Drug Delivery Reviews, No. 60, pp. 1117-1136 (Mar. 2008).
Schad et al., "In Vitro Characterization of Perfluorocarbon Droplets for Focused Ultrasound Therapy," Physics in Medicine and Biology, vol. 55, pp. 4933-4947 (2010).
Schoppee et al., "Chromatin Immunoprecipitation (ChiP): Revisiting the Efficacy of Sample Preparation, Sonication, Quantification of Sheared DNA, and Analysis via PCR," PLoS One, vol. 6, Issue 10, e26015, pp. 1-10 (Oct. 2011).
Schroeder et al., "Ultrasound Triggered Release of Cisplatin from Liposomes in Murine Tumors," Journal of Controlled Release, vol. 137, pp. 63-68 (2009).
Schumann et al., "Targeted-Microbubble Binding Selectively to GPIIb IIIa Receptors of Platelet Thrombi," Investigative Radiology, vol. 37, No. 11, pp. 587-593 (Nov. 2002).
Seed et al., "Representation of DNA Sequences in Recombinant DNA Libraries Prepared by Restriction Enzyme Partial Digestion," Gene, vol. 19, pp. 201-209 (Jun. 1982).
Selfridge et al., "KLM Transducer Model Implementation Using Transfer Matrices," IEEE Ultrasonics Symposium, pp. 875-877 (1985).
Sheeran et al., "Design of Ultrasonically-Activatable Nanoparticles using Low Boiling Point Perfluorocarbons," Biomaterials, vol. 33, No. 11, pp. 1-21 (Apr. 2012).
Sheeran et al., "Formulation and Acoustic Studies of a New Phase-Shift Agent for Diagnostic and Therapeutic Ultrasound," Langmuir, vol. 27, No. 17, pp. 1-23 (Sep. 6, 2011).
Sheeran et al., "Decafluorobutane as a Phase-Change Contrast Agent for Low-Energy Extravascular Ultrasonic Imaging," Ultrasound in Medicine and Biology, vol. 37, No. 9, pp. 1518-1530 (2011).
Shortencarier et al., "A Method for Radiation-Force Localized Drug Delivery Using Gas-Filled Lipospheres", IEEE Transactions on Ultrasonics, Ferroelectrics and Frequency Control, vol. 51, No. 7, pp. 822-831 (Jul. 2004).
Sirsi et al., "Microbubble Compositions, Properties and Biomedial Applications," Bubble Sci. Eng. Technol., vol. 1, , pp. 1-28 (Nov. 2009).

(56) References Cited

OTHER PUBLICATIONS

Staub et al., "Contrast-Enhanced Ultrasound Imaging of the Vasa Vasorum: From Early Atherosclerosis to the Identification of Unstable Plaques," J. Am. Coll. Cardiol. Img., vol. 3, No. 7, pp. 761-771 (Jul. 2010).
Stephens et al., "Efficient Array Design for Sonotherapy," Phys Med Biol., vol. 53, No. 14, pp. 1-42 (Jul. 21, 2008).
Stephens et al., "Multi-frequency Array Development for Drug Delivery Therapies: Characterization and First Use of a Triple Row Ultrasound Probe," IEEE Ultrasonics Symposium, pp. 66-69 (2006).
Stieger et al., "Enhancement of Vasular Permeability with Low-Frequency Contrast-Enhanced Ultrasound in the Chorioallantoic Membrane Model," Radiology, vol. 243, No. 1, pp. 112-121 (Apr. 2007).
Streeter et al., "Improving Sensitivity in Ultrasound Molecular Imaging by Tailoring Contrast Agent Size Distribution: In Vivo Studies," Molecular Imaging, vol. 9, No. 2, pp. 1-18 (Apr. 2010).
Stride et al., "Cavitation and Contrast: The Use of Bubbles in Ultrasound Imaging and Therapy," Proceedings of the Institution of Mechanical Engineers, Part H: Journal of Engineering in Medicine, vol. 224, pp. 171-191 (2010).
Talu et al., "Needle Size and Injection Rate Impact Microbubble Contrast Agent Population," Ultrasound in Medicine & Biology, vol. 34, No. 7, pp. 1-8 (Jul. 2008).
Talu et al., "Maintaining Monodispersity in a Microbubble Population Formed by Flow-Focusing," Langmuir, vol. 24, No. 5, pp. 1-14 (Mar. 2008).
Talu et al., "Tailoring the Size Distribution of Ultrasound Contrast Agents: Possible Method for Improving Sensitivity in Molecular Imaging," Molecular Imaging, vol. 6, No. 6, pp. 1-19 (2007).
Talu et al., "Long-Term Stability by Lipid Coating Monodisperse Microbubbles Formed by a Flow-Focusing Device," Langmuir, vol. 22, No. 23, pp. 1-10 (Nov. 7, 2006).
Tartis et al., "Therapeutic Effects of Paclitaxel-Containing Ultrasound Contrast Agents," Ultrasound in Medicine and Biology, vol. 32, No. 11, pp. 1771-1780 (2006).
Ten Kate et al., "Molecular Imaging of Inflammation and Intraplaque Vasa Vasorum: A Step Forward to Identification of Vulnerable Plaques", Journal of Nuclear Cardiology, vol. 17, pp. 897-912 (2010).
Teytelman et al., "Impact of Chromatin Structures on DNA Processing for Genomic Analyses," PLoS One, vol. 4, Issue 8, e6700, pp. 1-11 (Aug. 2009).
Thorstenson et al., "An Automated Hydrodynamic Process for Controlled, Unbiased DNA Shearing," Genome Research, vol. 8, pp. 848-855 (Aug. 1998).
Torchilin, "Passive and Active Drug Targeting: Drug Delivery to Tumors as an Example," Handbook of Experimental Pharmacology, pp. 3-53 (2010).
Tortoli et al., "Unexpected Doppler Effects from Microbubbles Moving Through an Ultrasound Beam," IEEE Ultrasonics Symposium, vol. 2, pp. 1729-1732 (1999).
Ueda et al., "Acoustic Cavitation as an Enhancing Mechanism of Low-Frequency Sonophoresis for Transdermal Drug Delivery," Biol. Pharm. Bull, vol. 32, No. 5, pp. 916-920 (2009).
Unger et al., "Therapeutic Applications of Lipid-Coated Microbubbles," Advanced Drug Delivery Reviews, vol. 56, pp. 1291-1314 (2004).
Unger et al., "Therapeutic Applications of Microbubbles," European Journal of Radiology, vol. 42, pp. 160-688 (2002).
Unger et al., "Local Drug and Gene Delivery Through Microbubbles," Progress in Cardiovascular Diseases, vol. 44, No. 1, pp. 45-54 (Jul./Aug. 2001).
Unger et al., "In Vitro Studies of a New Thrombus-Specific Ultrasound Contrast Agent," Am J Cardiol, vol. 81, No. 12A, pp. 58G-61G (1998).
van Wamel et al., "Vibrating Microbubbles Poking Individual Cells: Drug Transfer Into Cells via Sonoporation," Journal of Controlled Release, vol. 112, pp. 149-155 (2006).
Villanueva, "Molecular Imaging of Cardiovascular Disease Using Ultrasound," J. Nucl. Cardiol., vol. 15, No. 4, pp. 1-18 (2008).
Villanueva et al., "Microbubbles Targeted to Intracellular Adhesion Molecule-1 Bind to Activated Coronary Artery Endothelial Cells," Circulation, vol. 98, pp. 1-6 (1998).
Vorkurka, "Comparison of Rayleigh's, Herring's, and Gilmore Models of Gas Bubbles," Acustica, vol. 59, pp. 214-219 (1986).
Wang et al., "Controllable Microfludic Production of Multicomponent Multiple Emulsions," Lab Chip, vol. 11, pp. 1587-1592 (Mar. 9, 2011).
Ward et al., "Experimental Study of the Effects of Optison Concentration on Sonoporation In Vitro," Ultrasound in Medicine & Biology, vol. 26, No. 7, pp. 1169-1175 (May 2, 2000).
Watanabe et al., "Translational and Radical Motions of a Bubble in an Acoustic Standing Wave Field," Phys. Fluids A, vol. 5, No. 11, pp. 2682-2688 (Nov. 1993).
Wei et al., "Recent Advances in Myocardial Contrast Echoardiography," Curr. Opin. Cardiol., vol. 12, pp. 539-546 (1997).
Whitworth, "Discussion of One-D Piezoelectric Transducer Models With Loss," IEEE Transactions on Ultrasonics, Ferroelectrics and Frequency Control, vol. 48, No. 3, pp. 844-846 (May 2001).
Wigle et al., "Screening for Inhibitors of Low-Affinity Epigenetic Peptide-Protein Interactions: An AlphaScreen™-Based Assay for Antagonists of Methyl-Lysine Binding Proteins," Journal of Biomolecular Screening, vol. 15, No. 1, pp. 62-71 (2010).
Wilson et al., "Microbubble-Enhanced US in Body Imaging: What Role?," Radiology, vol. 257, No. 1, pp. 24-39 (Oct. 2010).
Wong et al., "Bubble Evolution in Acoustic Droplet Vaporization at Physiological Temperature via Ultra-high Speed Imaging," Soft Matter, vol. 7, pp. 4009-4016 (Jan. 2011).
Wong et al., "A Novel Method for Producing Partial Restriction Digestion of DNA Fragments by PCR with 5-methyl-CTP," Nucleic Acids Research, vol. 25, No. 20, pp. 4169-4171 (1997).
Wright et al., "Evaluation of New Thrombus-Specific Ultrasound Contrast Agent," Acad Radiol, vol. 5 (supp 1), pp. S240-S242 (1998).
Wu et al., "PSPICE Approach for Designing the Ultrasonic Piezoelectric Transducer for Medical Diagnostic Applications," Sensors and Actuators, vol. 75, pp. 186-198 (1999).
Xu et al., "Controllable Preparation of Monodisperse O/W and W/O Emulsions in the Same Microfluidic Device," Langmuir, vol. 22, No. 19, pp. 7943-7946 (Sep. 12, 2006).
Xu et al., "Generation of Monodisperse Particles by Using Microfluidics: Control Over Size, Shape, and Composition," Angew. Chem. Int. Ed., vol. 44, pp. 724-728 (2005).
Yasuda et al., "Using Acoustic Radiation Force as a Concentration Method for Erythrocytes," J. Acoust. Soc. Am., vol. 102, No. 1, pp. 642-645 (Jul. 1997).
Zhang et al., "Acoustic Droplet Vaporization for Enhancement of Thermal Ablation by High Intensity Focused Ultrasound," Acad Radiol., vol. 18, No. 9, pp. 1-20 (Sep. 2011).
Zhang et al., "Initial Investigation of Acoustic Droplet Vaporization for Occlusion in Canine Kidney," Ultrasound Med Biol., vol. 36, No. 10, pp. 1-33 (Oct. 2010).
Zhang et al., "An in Vitro Study of a Phase-Shift Nanoemulsion: A Potential Nucleation Agent for Bubble-Enhanced HIFU Tumor Ablation," Ultrasound in Med. & Biol., vol. 36, No. 11, pp. 1856-1866 (2010).
Zhao et al., "Selective Imaging of Adherent Targeted Ultrasound Contrast Agents," Physics in Medicine and Biology, vol. 52, pp. 2055-2072 (2007).
Zhao et al., "Radiation-Force Assisted Targeting Facilitates Ultrasonic Molecular Imaging," Molecular Imaging, vol. 3, No. 3, pp. 135-148 (Jul. 2004).
Zheng et al., "A Novel Sensitive Targeted Imaging Technique for Ultrasonic Molecular Imaging," IEEE 2007 Ultrasonics Symposium, pp. 957-960 (2007).
Zheng et al., "Ultrasound-Driven Microbubble Oscillation and Translation Within Small Phantom Vessels," Ultrasound in Med. & Biol., vol. 33, No. 12, pp. 1978-1987 (2007).

(56) References Cited

OTHER PUBLICATIONS

Zhou et al., "The Size of Sonoporation Pores on the Cell Membrane," Ultrasound in Medicine & Biology, vol. 35, No. 10, pp. 1-10 (Oct. 2009).
Zipparo, "Mid- to High-Power Ultrasound Imaging Arrays—from ARFI to HIFU," IEEE 2003 Ultrasonics Symposium; Honolulu, Hawaii, pp. 684-688 (2003).
Non-Final Office Action for U.S. Appl. No. 13/876,165 (Jun. 10, 2015).
Restriction/Election Requirement for U.S. Appl. No. 14/432,747 (Jun. 3, 2016).
Notice of Allowance, Examiner-Initiated Interview Summary, and AFCP 2.0 Decision for U.S. Appl. No. 13/876,165 (Apr. 28, 2016).
Applicant-Initiated Interview Summary for U.S. Appl. No. 13/876,165 (Mar. 28, 2016).
Commonly-assigned, co-pending PCT International Patent Application No. PCT/US2016/014685 for "Apparatuses, Systems, and Methods for Preclinical Ultrasound Imaging of Subjects," (Unpublished, filed Jan. 25, 2016).
Final Office Action for U.S. Appl. No. 13/876,165 (Dec. 31, 2015).
Notification of Transmittal of the International Search Report and the Written Opinion of the International Searching Authority, or the Declaration for PCT International Application No. PCT/US2014/064889 (Apr. 9, 2015).
Ainslie et al., "Review of scattering and extinction cross-sections, damping factors, and resonance frequencies of a spherical gas bubble," The Journal of the Acoustical Society of America, vol. 130, pp. 3184-3208 (2011).
Apfel, "Activatable infusable dispersions containing drops of a superheated liquid for methods of therapy and diagnosis," (1998).
Asami et al., "Acoustic Signal Characterization of Phase Change Nanadroplets in Tissue-Mimicking Phantom Gels," Jpn. J. Appl. Phys., vol. 49 (2010).
Asami et al., "Repeatable vaporization of optically vaporizable perfluorocarbon droplets for photoacoustic contrast enhanced imaging," 2012 IEEE International Ultrasonics Symposium (IUS), pp. 1200-1203 (2012).
Bekeredjian et al., "Therapeutic Use of Ultrasound Targeted Microbubble Destruction: A Review of Non-Cardiac Applications," Ultraschall in Med, vol. 27, pp. 134-140 (2006).
Calderon et al., "A boundary element model of the ransport of a semi-infinite bubble through a microvessel birfurcation," Physics of Fluids, vol. 22, p. 11 (2010).
Campbell, "Tumor Physiology and Delivery of Nanopharmaceuticals," Anti-Cancer Agents in Medicinal Chemistry, vol. 6, No. 6, pp. 503-512 (2006).
Choi et al., "Spatiotemporal evolution of cavitation dynamics exhibited by flowing microbubbles during ultrasound exposure," The Journal of te Acoustical Society of America, vol. 132, pp. 3538-3549 (2012).
Clarke et al., "Production of harmonics in vitro by high-intensity focused ulrasound," Ultrasound in Medicine Biology, vol. 25, pp. 1417-1424 (1999).
Coussios et al., "Applications of acoustics and cavitation to non-invasive therapy and drug delivery," Annual Review of Fluid Mechanics, vol. 40, pp. 395-420 (2008).
Couture et al., "Ultrasound inernal tattooing," Medical Physics, vol. 38, pp. 1116-1123 (2011).
D'Astous et al., "Frequency dependence of ultrasound attenuation and backscatter in breast tissue," Ultrasound in Medicine Biology, vol. 12, pp. 795-808 (1986).
Dayton et al., "Molecular ultrasound imaging using microbubble contrast agents," Frontiers in Bioscience, vol. 12, pp. 5124-5142 (Sep. 1, 2007).
Eshpuniyani et al., "A boundary element model of microbubble sticking and sliding in the microcirculation," International Journal of Heat and Mass Transfer, vol. 51, pp. 5700-5711 (2008).
Forsberg et al., "Subharmonic imaging of contrast agents," Ultrasonics, vol. 38, pp. 93-98 (2000).

Gramiak et al., "Echocardiography of the aortic root," Invest. Radiol., vol. 3, pp. 356-366 (1968).
Hurrell, "Voltage to pressure conversion: are you getting 'phased' by the problem?," Journal of Physics: Conference Series, vol. 1, p. 57 (2004).
ten Kate et al., "Molecular imaging of inflammation and intraplaque vasa vasorum: a step forward to identification of vulnerable plaques?," J. Nucl. Cardiol., vol. 17, pp. 897-912 (2010).
"Definity®," Lantheus Medical Imaging. WayBack Machine https://web.archive.org/web/20101123011336/http://www.definityimaging.com/main.html? (Nov. 23, 2010).
Lediju et al., "Short-lag spatial coherence imaging," 2010 IEEE International Ultrasonics Symposium, pp. 987-990 (2010).
Martin et al., "Current status and prospects for microbubbles in ultrasound theranostics," Wiley Interdisciplinary Reviews: Nanomedicine and Nanobiotechnology, vol. 5. pp. 329-345 (2013).
Minnaert, "On musical air-bubbles and the sounds of running water," Philosophical Magazine, vol. 16, pp. 235-248 (1933).
Misaridis et al., "Use of modulated excitation signals in medical ultrasound. Part 1: Basic concepts and expected benefits," IEEE Transactions on Ultrasonics Ferroelectronics and Frequency Control, vol. 52, pp. 177-191 (2005).
Needles et al., "Nonlinear contrast imaging with an array-based micro-ultrasound system," Ultrasound in Medicine & Biology, vol. 36, pp. 2097-2106 (2010).
Okpodu et al., "Rapid Isolation of Nuclei From Carrot Suspension Culture Cells Using a BioNebulizer," BioTechniques, vol. 16, No. 1, pp. 154-158 (1994).
Pitt et al., "Phase Transitions of Perfluorocarbon Nanoemulsion Induced with Ultrasound: A Mathematical Model," Ultrasonics Sonochemistry, vol. 21, pp. 879-891 (2014).
Qamar et al., "Evolution of acoustically vaporized microdroplets in gas embolotherapy," Journal of Biomechanical Engineering, vol. 134, pp. 031010-1-031010-13 (2012).
Rapoport, "Phase-shift, stimuli-responsive perfluorocarbon nanodroplets for drug delivery to cancer," Wiley Interdisciplinary Reviews: Nanomedicine and Nanobiotechnology, vol. 4, pp. 492-510 (2012).
Rapoport et al., "Ultrasound-mediated tumor imaging and nanotherapy using drug loaded, block copolymer stabilized perfluorocarbon nanoemulsions," Journal of Controlled Release, vol. 153, pp. 4-15 (2011).
Reznik et al., "The efficiency and stability of bubble formation by acoustic vaporization of submicron perfluorocarbon droplets," Ultrasonics, vol. 53, pp. 1368-1376 (2013).
Reznik et al., "Investigation of Vaporized Submicron Perfluorocarbon Droplets as an Ultrasound Contrast Agent," Ultrasound in Medicine & Biology, vol. 37, pp. 1271-1279 (2011).
Salgaonkar et al., "Passive cavitation imaging with ultrasound arrays," The Journal of the Acoustical Society of America, vol. 126, pp. 3071-3083 (2009).
Sassaroli et al., Cavitation threshold of microbubbles in gel tunnels by focused ultrasound, Ultrasound in Medicine Biology, vol. 33, pp. 1651-1660 (2007).
Sheeran et al., "Vaporization phenomena for ultrasound phase-change contrast agents assessed via high-speed optical microscopy," 2013 IEEE International Ultrasonics Symposium (IUS), pp. 1841-1844 (Jul. 21-25, 2013).
Sheeran et al., "Toward ultrasound molecular imaging with phase-change contrast agents: an in vitro proof of principle," Ultrasound Med. Biol., vol. 39, No. 5, pp. 893-902 (May 2013).
Sheeran et al., "Phase-transition thresholds and vaporization phenomena for ultrasound phase-change nanoemulsions assessed via high-speed optical microscopy," Physics in Medicine and Biology, vol. 58, p. 4513 (2013).
Sheeran et al., "Phase-change contrast agents for imaging and therapy," Curr. Pharm. Des., vol. 18, pp. 2152-2165 (2012).
Sheeran et al., "Perflourobutane as a Phase-Change Contrast Agent for Low-Energy Extravascular Ultrasound Imaging," pp. 1-8 (Publication Date Unknown).
Shpak et al., "Ultrafast dynamics of the acoustic vaporization of phase-change microdroplets," Journal of the Acoustical Society of America, vol. 134, pp. 1610-1621 (2013a).

(56) References Cited

OTHER PUBLICATIONS

Shpak et al., "The role of gas in ultrasonically driven bapor bubble growth," Physics in Medicine and Biology, vol. 58, pp. 2523-2535 (2013b).

Strohm et al., "Vaporization of perfluorocarbon droplets using optical irradiation," Biomed. Opt. Express, vol. 2, pp. 1432-1442 (2011).

Whittingham, "Contrast-specific imaging techniques: technical perspective," Contrast Media in Ultrasonography: Basic Prinicples and Clinical Applications, pp. 43-70 (2005).

Wilson et al., "Biomedical photoacoustics beyond thermal expansion using triggered nanodroplet vaporization for contrast-enhanced imaging," Nature Communications, vol. 3, p. 618 (2012).

Ye et al., "Microbubble Expansion in a Flexible Tube," Transactions of the ASME, vol. 128, pp. 554-563 (Aug. 2006).

Ye et al., "Direct Numerical Simulations of Micro-Bubble Expansion in Gas Embolotherapy," Journal of Biomedical Engineering, vol. 126, pp. 745-759 (Dec. 2004).

Notification of Transmittal of the International Search Report and the Written Opinion of the International Searching Authority, or the Declaration for International Application No. PCT/US2016/014685 (Jun. 30, 2016).

\* cited by examiner

SYSTEMS, METHODS, AND COMPUTER READABLE MEDIA FOR HIGH FREQUENCY CONTRAST IMAGING AND IMAGE-GUIDED THERAPEUTICS

PRIORITY CLAIM

This application claims the benefit of U.S. Provisional Patent Application Ser. No. 61/240,166, filed Sep. 4, 2009; the disclosure of which is incorporated herein by reference in its entirety.

GOVERNMENT INTEREST

This presently disclosed subject matter was made with U.S. Government support under Grant No. 1R01EB009066-01 awarded by the National Institutes of Health. Thus, the U.S. Government has certain rights in the presently disclosed subject matter.

TECHNICAL FIELD

The subject matter described herein relates to methods and systems using ultrasonic imaging. More particularly, the subject matter described herein relates to systems, methods, and computer readable media for high-frequency contrast imaging and image-guided therapeutics.

BACKGROUND

With recent advances in animal models of disease, there has been great interest in capabilities for high-resolution ultrasound imaging. High-resolution ultrasound imaging is performed at high frequencies, typically greater than 15 MHz, whereas clinical ultrasound imaging is typically in the 1-15 MHz range. Higher frequencies are proportional to higher resolution.

High-frequency ultrasound is a popular modality for imaging animal models of human disease because of its portability, relatively low cost, and real-time imaging capability. High frequency ultrasound (>15 MHz) is different from traditional clinical ultrasound because of its high resolution capability, although with the sacrifice of penetration depth. Encapsulated microbubbles are often implemented as contrast agents during these ultrasound studies to improve detection of blood flow. Their use requires an intravascular injection of a solution of microbubbles immediately prior to an imaging exam. After their injection, the microbubble contrast agents (MCAs) traverse the circulatory system with similar rheology to erythrocytes. The acoustic impedance mismatch between MCA gas cores and the surrounding blood and tissue is significant—approximately four orders of magnitude—causing them to scatter ultrasound and thus enhance the image intensity in their vicinity extremely efficiently.

The most basic method of microbubble contrast enhanced ultrasound relies on receiving the acoustic signal scattered from them at the fundamental imaging frequency. One limitation to this detection method is that echoes from both tissue and MCAs are in the same frequency band. This necessitates a large quantity of injected MCAs to compete with the inherent and unwanted tissue backscatter. However, owing to the broadband and nonlinear acoustic responses of these gas-filled spheres it is possible to overcome this limitation with other detection strategies. The most powerful MCA imaging methods are derived from their nonlinear responses to ultrasound, providing MCAs distinct differences in their echo signatures when compared to the linear responses of tissue and blood. Imaging modes such as subharmonic imaging, and phase inversion exploit MCAs' nonlinear response and provide improved contrast-to-tissue ratios compared to the previously described fundamental mode imaging. Although these nonlinear imaging methods are now widely utilized in commercial ultrasound systems operating in the 1-15 MHz range, they have yet to be implemented efficiently in high frequency ultrasound systems. One likely reason for this is that optimal MCA response requires excitation near the resonant frequency, which is typically in the 0.5-8 MHz range for bubbles of several microns in diameter and the range in which most commonly available commercially produced MCAs fall.

The ability to detect small numbers of contrast agents in a tissue background is particularly important for molecular imaging or perfusion imaging. MCAs are unique in that they scatter ultrasound energy at higher and lower harmonics than the fundamental imaging frequency. These broadband harmonics, due to the contrast agents' nonlinear response, have been shown to be most intense when insonified near the MCAs' resonant frequencies. To date, efficiently exciting harmonic response has not been possible with high-frequency imaging systems since most contrast agents are resonant in the 1-5 MHz frequency range.

Thus, there exists a need for systems which can excite microbubble contrast agents efficiently, and also detect them with a high-frequency system for high-resolution imaging.

Additionally, there has been an interest in the application of ultrasound to enhance drug and gene delivery. There are several mechanisms whereby this might occur. One mechanism is the use of radiation force (RF) to enhance both diagnostic and therapeutic ultrasound (US) imaging studies. RF pulses have shown to enhance adhesion of targeted MCAs, thus improving their signal to noise ratio. RF has also been shown to be effective in concentrating therapeutic delivery vehicles at desired locations as determined by the ultrasound focus, thereby providing a mean for ultrasound-directed, site-specific drug delivery. The magnitude of RF on MCAs is maximized when generated near their resonance frequency, typically in the 1-5 MHz range. Traditional high frequency imaging transducers are therefore not optimized to produce RF on most MCAs.

Thus, there exists a need to simultaneously image with high resolution (high frequency), and use low frequency energy to produce radiation force at the desired site, as selected by imaging.

In addition, ultrasound can mediate local drug delivery by disrupting drug-carrier vehicles, causing enhanced release of contents. Low frequency ultrasound has also been shown to locally increase vascular or cell membrane permeability, and to enhance gene transfection. These abilities are of particular interest for small animal studies, where much of the work in US molecular imaging and therapeutic delivery is being tested. However, all of these effects have been shown to occur primarily at low frequencies, typically in the 1-2 MHz range. Thus, it is not possible to mediate these therapeutic effects with a standard high frequency transducer.

Accordingly, in light of these disadvantages associated with conventional ultrasonic imaging systems, there exists a need for systems, methods, and computer readable media for high-frequency contrast imaging and image-guided therapeutics.

SUMMARY

This invention encompasses an ultrasonic transducer, imaging strategies, and software control to implement these imaging strategies for high-frequency ultrasound contrast imaging and image-guided therapeutic approaches using high-frequency ultrasound imaging to guide therapy.

According to one aspect, the subject matter described herein includes a system for high frequency contrast imaging and image-guided therapeutics, the system including an ultrasound transducer operable to transmit ultrasound at a first frequency bandwidth and receive ultrasound at a second frequency bandwidth different from the first frequency bandwidth, and a control module for controlling the ultrasound transducer to provide ultrasound of the first frequency bandwidth, directed toward a volume to be imaged, the volume containing a carrier having non-linear acoustical properties. The ultrasound of the first frequency bandwidth causes the carrier to generate ultrasound of a second frequency bandwidth. The ultrasound transducer receives ultrasound of the second frequency bandwidth from the volume to be imaged, and the control module uses the received ultrasound of the second frequency bandwidth to generate an image of the volume to be imaged. The components of the second frequency bandwidth that are detected are of a frequency greater than 20 MHz.

According to another aspect, the subject matter described herein includes a method for high frequency contrast imaging and image-guided therapeutics. The method includes providing ultrasound of a first frequency bandwidth, directed toward the volume to be imaged, the volume containing a carrier having non-linear acoustical properties, wherein the ultrasound of the first frequency bandwidth causes the carrier to generate ultrasound of a second frequency bandwidth that is different from the first frequency bandwidth, and receiving, from the volume to be imaged, ultrasound of the second frequency bandwidth. The received ultrasound of the second frequency bandwidth is used to generate an image of the volume to be imaged. The components of the second frequency bandwidth that are detected are of a frequency greater than 20 MHz.

The subject matter described herein for high-frequency contrast imaging and image-guided therapeutics may be implemented in hardware, software, firmware, or any combination thereof. As such, the terms "function" or "module" as used herein refer to hardware, software, and/or firmware for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As used herein, the term "contrast agents" refers to gas-filled particles, stabilized by a lipid, protein, or polymer shell, or to liquid-filled particles, stabilized by a lipid, protein, or polymer shell, where the liquid has an impedance mismatch of at least a factor of 2 from that of blood plasma.

As used herein, the terms "drug delivery vehicles" and "drug carrier vehicles" refer to gas-filled particles, stabilized by a lipid, protein, or polymer shell, which also include a therapeutic compound either within the shell, or attached to the shell. These terms refer also to liquid-filled particles, stabilized by a lipid, protein, or polymer shell, where the liquid has an impedance mismatch of at least a factor of 2 from that of blood plasma, and a therapeutic compound is included either within the liquid core or attached to the shell.

As used herein, the terms "gene delivery vehicles" and "gene carrier vehicles" refer to gas-filled particles, stabilized by a lipid, protein, or polymer shell, which also include a plasmid, virus, or small interfering RNA (siRNA) either within the shell, or attached to the shell. These terms refer also to liquid-filled particles, stabilized by a lipid, protein, or polymer shell, where the liquid has an impedance mismatch of at least a factor of 2 from that of blood plasma, and a plasmid, virus, or siRNA is included either within the liquid core or attached to the shell.

BRIEF DESCRIPTION OF THE DRAWINGS

Preferred embodiments of the subject matter described herein will now be explained with reference to the accompanying drawings, wherein like reference numerals represent like parts, of which.

DETAILED DESCRIPTION

Figure 1:
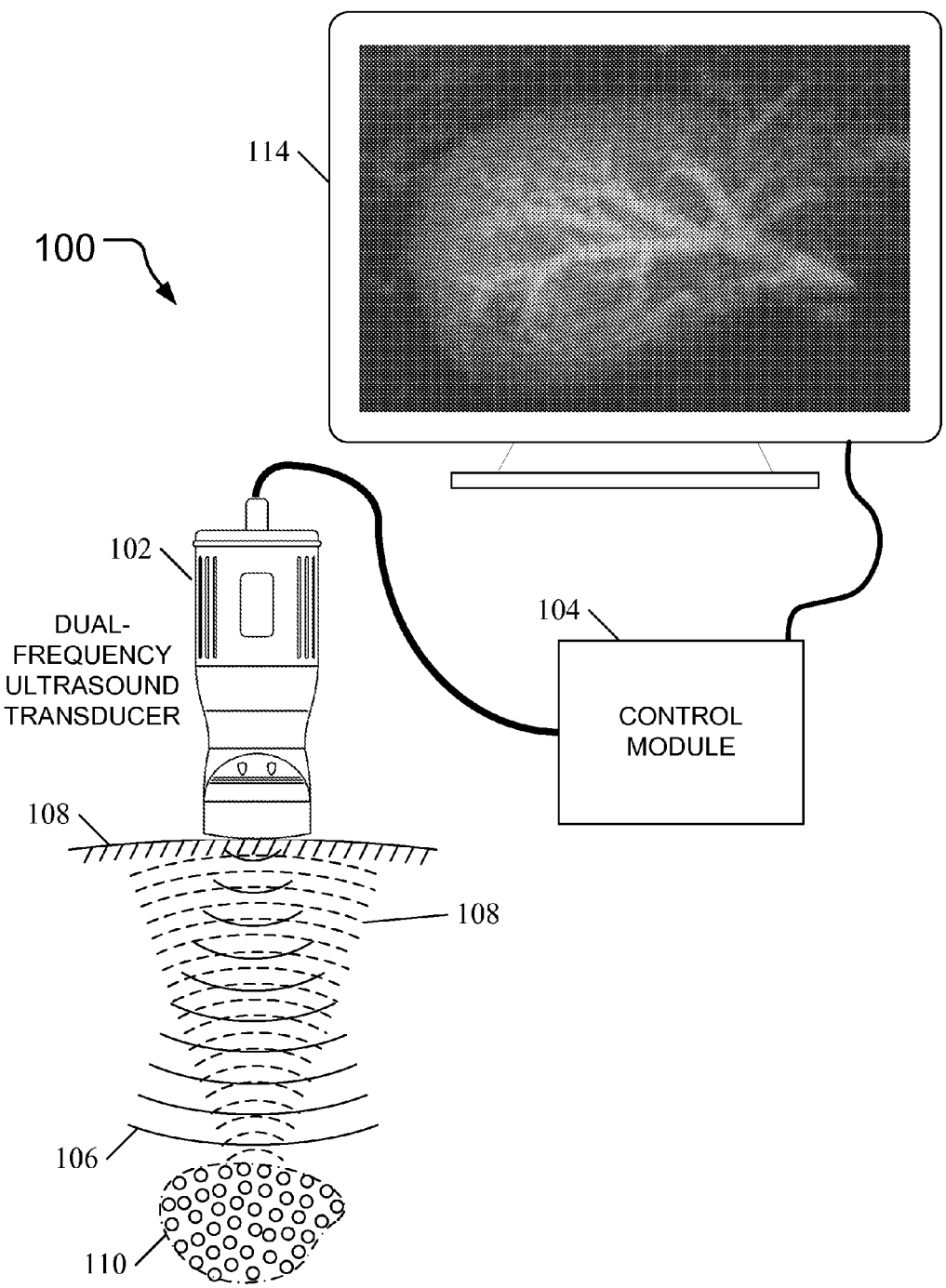
FIG. 1 is a block diagram illustrating a system for high frequency contrast imaging and image-guided therapeutics according to an embodiment of the subject matter described herein.

FIG. 1 is a block diagram illustrating a system for high frequency contrast imaging and image-guided therapeutics according to an embodiment of the subject matter described herein. In the embodiment illustrated in FIG. 1, system 100 includes an ultrasound transducer 102 (which may also be referred to as "ultrasonic transducer 102" or simply "transducer 102") operable to transmit ultrasound at a first frequency bandwidth and receive ultrasound at a second frequency bandwidth different from the first frequency bandwidth. In one embodiment, transducer 102 may be a dual-frequency or multi-frequency ultrasound transducer. System 100 also includes a control module 104 for controlling transducer 102 to provide ultrasound of the first frequency bandwidth 106, directed toward a volume to be imaged 108. Volume to be imaged 108 contains a carrier 110 having non-linear acoustical properties, shown in FIG. 1 as a portion or sub-volume of volume to be imaged 108, the sub-volume containing a number of microbubble contrast agents. Ultrasound of the first frequency bandwidth 106 causes carrier 110 to generate ultrasound of a second frequency bandwidth 112. Transducer 102 receives ultrasound of the second frequency bandwidth 112 from volume to be imaged 108. This received ultrasound is used to generate an image 114 of volume to be imaged 108. In one embodiment, transducer 102 may generate a low-frequency bandwidth 106, which causes carrier 110 to generate a high-frequency bandwidth 112, which is detected by transducer 102.

In one embodiment, the components of ultrasound of the second frequency bandwidth 112 that are detected by transducer 102 are of a frequency greater than 20 MHz. In alternative embodiments, the components of ultrasound of the second frequency bandwidth 112 that are detected by transducer 102 are of a frequency greater than 20 MHz, such as greater than 25 MHz or even higher frequencies.

Examples of carrier 110 include, but are not limited to, an acoustically active liposphere, a liposome, a gas-filled agent, a liquid perfluorocarbon droplet, and a contrast agent. Carrier 110 may also be a substance having an acoustical property, such as acoustic impedance, for example, that is different from an acoustical property of biological tissue. Carrier 110 may be or contain a therapeutic compound. In one embodiment, carrier 110 may have an outer surface having one or more molecular structures for attaching the carrier to biological structures or that target a cell receptor or multiple cell receptors.

Figure 2:
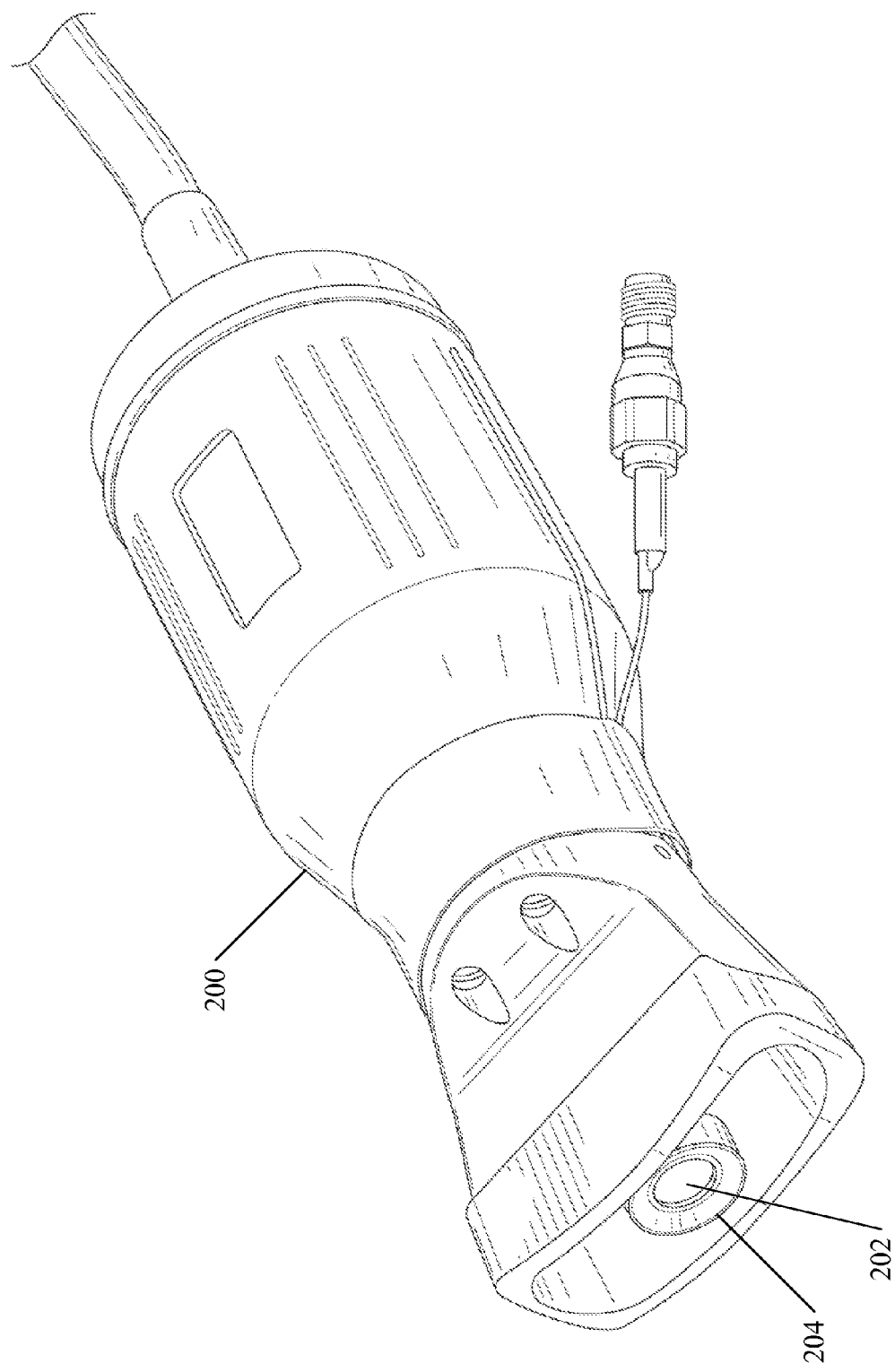
FIG. 2 illustrates in more detail the structure of an exemplary ultrasound transducer according to an embodiment of the subject matter described herein.

FIG. 2 illustrates in more detail the structure of an exemplary ultrasound transducer according to an embodiment of the subject matter described herein. In the embodiment illustrated in FIG. 2, transducer 200 is a hand-held device having a high-frequency (HF) receiver 202 located in the center of a ring-shaped low-frequency (LF) transmitter 204. In alternative embodiments, high-frequency receiver 202 may be a high-frequency transceiver, i.e., capable of sending as well as receiving high-frequency ultrasound. Likewise, low frequency transmitter 204 may be a low-frequency transceiver capable of not only sending but also receiving low-frequency ultrasound. In one embodiment, transducer 200 may transmit ultrasound at both the first and second frequency bandwidths simultaneously.

For simplicity of explanation, the term "transducer" will hereinafter be used to refer to devices that may transmit ultrasound, devices that may receive ultrasound, or devices that both transmit and receive ultrasound.

Likewise, the term "multi-frequency transducer" will refer to a transducer that can transmit and/or receive signals in two or more frequency bandwidths. This term includes, but it not limited to, dual-frequency transducers. Although the examples given below may be addressed to dual-frequency transducers, the subject matter described herein is not so limited, but may be applied to triple-frequency transducers, quadruple-frequency transducers, and so on.

Alternative structures for the multi-frequency transducers are also contemplated. Structures for dual-frequency transducers, for example, include arrangements in which the LF and HF transducers are coplanar, stacked one above the other, or inter dispersed within each other (array based 1D, 1.5D, 2D, etc. . . . ) where their beams are co-registered or where the beam profiles are known with respect to each other. Examples of transducer technologies include piezoelectric stacks, capacitive micromachined ultrasonic transducers (CMUTS) and piezoelectric micromachined ultrasonic transducers (PMUTS). In one embodiment, the −12 dB bandwidths of the first and second frequency range do not overlap each other.

In one embodiment, the transducer is mechanically scanned, where excitation is switched between the low frequency and high frequency element on successive sweeps across the area to be imaged, or on alternate transmit lines. In one embodiment, the high frequency element receives the ultrasonic reflections from both the low frequency and high frequency sweeps, but the system encodes or presents the information acquired during the low frequency sweep differently from the information acquired during the high frequency sweep. For example, information acquired during the low frequency sweep may be presented in one color and information acquired during the high frequency sweep may be presented in another color. Likewise, information acquired during the low frequency sweep may be encoded differently from information acquired during the high frequency sweep. This allows the system to make a distinction between contrast agent and tissue, for example, and can generate an image where contrast agent and tissue are displayed in colors that are different from each other. The same techniques can be employed by a transducer that is not mechanically scanned, but rather is a multi-frequency array. Example dual-frequency arrays include transducers with multiple transceivers arranged in alternating rows or a checkerboard pattern, for example, or other array arrangements. The same techniques can be employed by transducers using phased arrays instead of using mechanisms to sweep or scan the transducer.

The technology described herein for dual-frequency ultrasound has several applications. One application is for high frequency (high resolution) contrast imaging with a large contrast-to-tissue ratio. By using two confocal transducers—a low frequency element to excite the bubbles near resonance and a high frequency element to receive scattered ultrasound from microbubbles—it is possible to simultaneously improve spatial resolution and suppress backscatter from tissue. Examples of volumes that would benefit from the imaging and image-guided therapeutics systems and methods described herein include, but are not limited to, veins, arteries, venules, arterioles, capillaries, and lymphatic structures. One embodiment of this process is described in FIG. 3.

Figure 3:
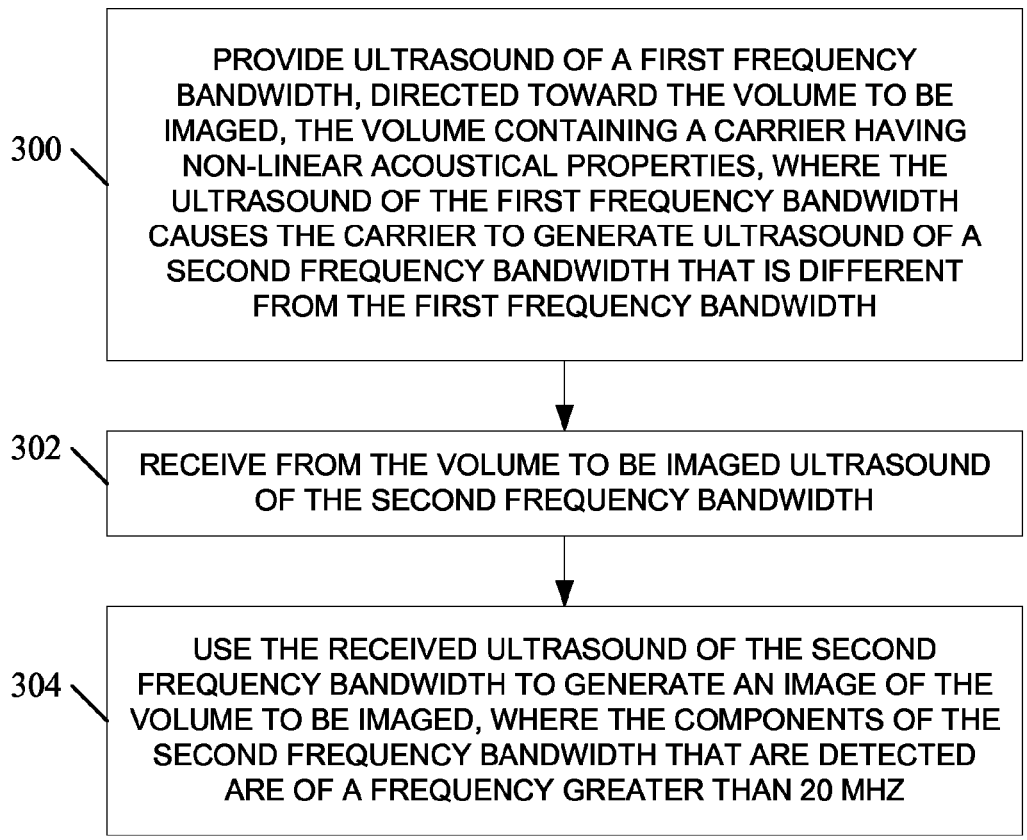
FIG. 3 is a flow chart illustrating an exemplary process for high-frequency contrast imaging and image-guided therapeutics according to an embodiment of the subject matter described herein.

FIG. 3 is a flow chart illustrating an exemplary process for high-frequency contrast imaging and image-guided therapeutics according to an embodiment of the subject matter described herein. This process will now be described with reference to FIGS. 1 and 3.

At block 300 of FIG. 3, ultrasound of a first frequency bandwidth is directed toward the volume to be imaged, the volume containing a carrier having non-linear acoustical properties. The ultrasound of the first frequency bandwidth causes the carrier to generate ultrasound of a second frequency bandwidth that is different from the first frequency bandwidth. For example, transducer 102 may direct ultrasound of the first frequency bandwidth 106 toward volume 108, which contains carrier 110. In one embodiment, carrier 110 is a contrast agent and transducer 102 generates a low-frequency ultrasonic bandwidth, which causes carrier 110 to generate a response in a high-frequency ultrasonic bandwidth.

At block 302, ultrasound of the second frequency bandwidth is received from the volume to be imaged. For example, ultrasound of the second frequency bandwidth 112 is received by transducer 102 from volume 108.

At block 304, the received ultrasound of the second frequency bandwidth is used to generate an image of the volume to be imaged, where the components of the second frequency bandwidth that are detected are of a frequency greater than 20 MHz. For example, the ultrasound received by transducer 102 is processed by control module 104 and used to produce an image 114, which is an image of the volume to be imaged 108. In one embodiment, the first frequency bandwidth has a center frequency in the range from 0.8 MHz to 10 MHz.

In one embodiment, the ultrasound of the first frequency bandwidth may be used to affect the position, size, or structural integrity of the carrier, to affect the proximity of the carrier relative to a target portion of the volume to be imaged, to affect vascular permeability of tissue in the volume to be imaged, or to affect the temperature within the volume to be imaged. In one embodiment, the ultrasound of the first frequency bandwidth may be used for sonophoresis.

Another application of this dual-frequency approach is for site-localized application of radiation force for enhancement of targeted imaging, or for enhanced delivery of drug delivery carriers. Acoustic radiation force is maximized near the resonant frequency of the microbubble (0.5-8 MHz range for bubbles of several microns in diameter), and therefore is not optimized at high-frequencies. However, the dual-frequency probe allows high-resolution imaging with simultaneous application of radiation force to a desired area. The desired area can be chosen with software with enables a region-of-interest to be selected on the high-frequency image, and then the low frequency transducer is activated to apply radiation force only in that region of interest. One embodiment of this process is described in FIG. 4.

Figure 4:
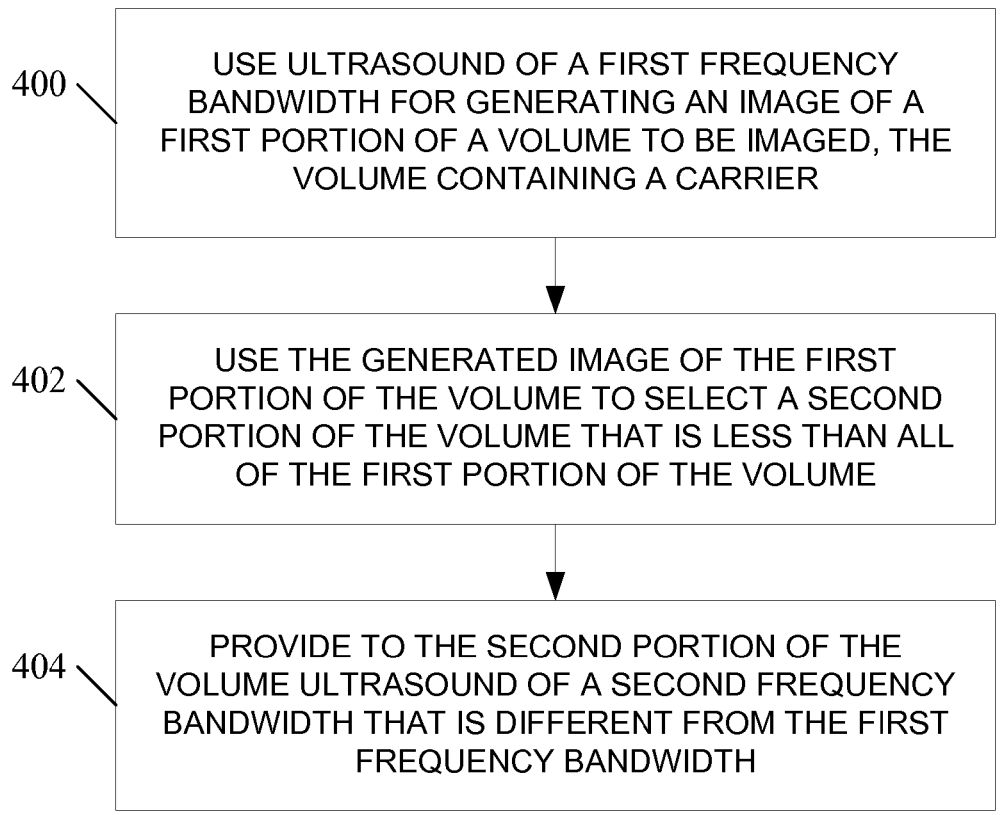
FIG. 4 is a flow chart illustrating an exemplary process for high-frequency contrast imaging and image-guided therapeutics according to another embodiment of the subject matter described herein.

FIG. 4 is a flow chart illustrating an exemplary process for high-frequency contrast imaging and image-guided therapeutics according to another embodiment of the subject matter described herein.

At block 400, ultrasound of a first frequency bandwidth is used to generate an image of a first portion of a volume to be imaged, the volume containing a carrier. In FIG. 1, for example, transducer 102 may use high frequency ultrasound to generate an image of a first portion of volume to be imaged 108, e.g., to generate an image of an organ.

At block 402, the generated image of the first portion of the volume is used to select a second portion of the volume that is less than all of the first portion of the volume. For example, a user of system 100 may select a portion of generated image 114, such as a diseased or damaged portion of an organ.

At block 404, ultrasound of a second frequency bandwidth that is different from the first frequency bandwidth is provided to the second portion of the volume. For example, transducer 102 may direct low frequency ultrasound to the selected portion of an organ. In one embodiment, the center frequency of the first frequency bandwidth is a higher frequency than the center frequency of the second frequency bandwidth. For example, in one embodiment the center frequency of the first frequency bandwidth is greater than or equal to 10 MHz. In one embodiment, the center frequency of the second frequency bandwidth is less than or equal to 10 MHz. In one embodiment, the −12 dB bandwidths of the first and second frequency range do not overlap each other.

In one embodiment, the ultrasound of the first frequency bandwidth may be used to affect the position, size, or structural integrity of the carrier, to affect the proximity of the carrier relative to a target portion of the volume to be imaged, to affect vascular permeability of tissue in the volume to be imaged, or to affect the temperature within the volume to be imaged. In one embodiment, the ultrasound of the first frequency bandwidth may be used for sonophoresis.

In one embodiment, carrier 110 may be a contrast agent, and ultrasound of the second frequency bandwidth may cause carrier 110 to generate ultrasound having at least some components within the first frequency bandwidth. For example, a first frequency bandwidth may be a high-frequency ultrasonic bandwidth that is used to generate an image of an organ containing a contrast agent. The second frequency bandwidth may be a low-frequency ultrasonic bandwidth that is used to direct carrier 110 to a desired location within the organ. The same or a different low-frequency ultrasonic bandwidth may cause carrier 110 to generate a high-frequency ultrasonic bandwidth response, which may be used to further enhance the image of the organ.

Yet another application of the dual- or multi-frequency transducer and software is for site-targeted drug and gene delivery. Ultrasonically mediated drug delivery (which may consist of microbubble or drug delivery vehicle rupture, sonoporation, or vascular permeability enhancement) and gene delivery, are all optimized at low frequencies (0.5-8 MHz), and typically closer to 0.5-2 MHz. The dual frequency probe approach allows high-resolution image-guided drug and gene delivery.

In one embodiment, the ultrasound of the second frequency bandwidth may be used to affect the position, size, or structural integrity of the carrier, to affect the proximity of the carrier relative to a target portion of the volume to be imaged, to affect vascular permeability of tissue in the volume to be imaged, or to affect the temperature within the volume to be imaged. In one embodiment, the ultrasound of the first frequency bandwidth may be used for sonophoresis.

This technology achieves a significant advance in the signal-to-noise ratio that a high-frequency ultrasound system (>15 MHz) can have for detection of ultrasound contrast agents. The technology also describes how high-frequency ultrasound can be used for ultrasound guidance for ultrasound-mediated therapy. In one embodiment, a dual-frequency ultrasound technique is used, in which a single transducer produces both low-frequency ultrasound (LFUS) and high-frequency ultrasound (HFUS). The boundary frequency that distinguishes a low-frequency US from a high-frequency US is not strictly defined, but typical applications place that boundary frequency in the 1-10 MHz range. Thus, in one application, LFUS means "less than 5 MHz" and HFUS means "greater than 5 MHz". In another application, LFUS may be less than 10 MHz while HFUS is greater than 10 MHz. In one embodiment of the subject matter described herein, detection and use of high frequency US having a frequency component at or above 20 MHz is presented.

Imaging. In one embodiment, a dual- or multi-frequency transducer generates LFUS in the range of 1-5 MHz to excite microbubbles near resonance and detect harmonic content above 25 MHz. Detection of energy at frequencies higher than the center frequency, such as detection of higher frequency harmonics, is herein referred to as "ultra-broadband imaging". This provides high sensitivity to contrast agents with high resolution and superior tissue rejection. Preliminary in vivo tests with this probe have been performed on rats. In one study, exemplary images of the animals' left kidneys were obtained for multiple bolus injections in both dual-frequency imaging mode and standard B-mode imaging mode, in which a linear array of transducers simultaneously scans a plane through the body that can be viewed as a two-dimensional image on screen. The resulting contrast-to-tissue ratios within the imaging regions of interest were determined offline and compared.

Additionally, susceptibility to tissue motion was compared against standard power Doppler imaging. This ultra-broadband imaging approach demonstrated spatial resolution near that of the high-frequency element (30 MHz), and contrast-to-tissue ratios 15 dB greater using the ultra-broadband imaging approach compared to standard 30 MHz B-mode. Ultra-broadband imaging is demonstrated to be not affected by tissue motion, since this method does not rely on detecting signal decorrelation or require background subtraction, unlike power Doppler or image-subtraction contrast imaging methods. Ultra-broadband imaging can be implemented on a high-resolution ultrasound system by utilizing a dual-frequency transducer, with a substantial improvement in contrast-to-tissue detection compared to B-mode imaging, and robustness in the presence of tissue motion compared to signal-subtraction or power-Doppler contrast detection techniques. This technology provides a substantial improvement in sensitivity for ultrasonic molecular imaging and slow-flow perfusion imaging in animal models.

Therapy.

In one embodiment, a dual- or multi-frequency transducer generates a HFUS signal in the 30 MHz range for high-resolution image guidance and a LFUS signal in the 1-4 MHz range for therapeutic use. Potential therapeutic uses include using radiation force to affect the location of carriers containing therapeutic compounds, such that the carriers are concentrated in an area to which the therapeutic compound is being targeted, e.g., a tumor site. The same transducer could be used to 'pop' or rupture the carrier bubbles, which delivers a particular dose of the therapeutic compound to the targeted area.

In one example application, biotinylated MCAs were injected through a 200 um cellulose tube coated with avidin. RF pulses lasting 10 s were delivered to the tube and the efficiency of this targeting was verified optically. Scattered US signals from free and targeted contrast agents were delineated by applying slow time filters to the radio frequency data. Additionally, the image intensities in the B-Mode images were compared in regions with and without the RF pulses. This technique is capable of pushing a polydisperse distribution of MCAs moving with a linear flow velocity of 44 mm/s a distance of 200 um perpendicular to their direction of motion and against buoyancy in 10 ms. Using a 10 second RF pulse, the probe has proven capable of improving the binding efficiency of freely flowing targeted MCAs in a localized area. Signal processing on the radio frequency data confirmed a localized region of enhanced signal intensity from increased adhesion of targeted contrast agents in the region of RF application. Signal processing of stationary echo signals from RF data allows display of targeted contrast agent signal overlaid with B-mode image data.

These effects were verified in-vivo, where the dual frequency transducer prototype utilized 30 MHz ultrasound to image a subcutaneous tumor in a rat. A molecularly-targeted microbubble vehicle was administered into the rodent's bloodstream through the tail vein, and then low frequency ultrasound at 2.5 MHz was administered to the tumor region for 30 seconds. The dual-frequency transducer enabled low-frequency ultrasound delivery to the tumor region via high-frequency image guidance. This resulted in a substantial increase in the delivery of the microbubble vehicles to the vasculature of the treated tumor. Ultrasound imaging, using the dual-frequency method (transmission at 2.5 MHz and reception with the 30 MHz element), before and after radiation force administration illustrated a 13 dB in signal enhancement in signal improvement, corresponding to this enhanced microbubble retention.

In one embodiment, an ultrasound dual- or multi-frequency transducer is provided having the capability to transmit energy to a volume at a low frequency (LF) (0.5-8 MHz), and simultaneously receive from this volume, or transmit and receive from this volume, at high frequencies (HF) (15-75 MHz). In one embodiment, the transducer could be a multi-element annular array, where one or more elements are low-frequency (0.5-5 MHz), and one or more elements are high frequency (15-75 MHz). Alternative embodiments of the dual-frequency transducer include: a linear array with a mixture of both low-frequency (0.5-8 MHz), and high-frequency (15-75 MHz) components; a phased array with a mixture of both low-frequency (0.5-8 MHz), and high-frequency (15-75 MHz) components; a 2-d matrix array, with a mixture of both low-frequency (0.5-8 MHz), and high-frequency (15-75 MHz) components; and a multi-layer transducer with a mixture of both low-frequency (0.5-8 MHz), and high-frequency (15-75 MHz) components.

In one embodiment, a dual frequency transducer is used to excite ultrasound contrast agents (defined as gas, liquid, or solid particles, from 100 nm-10 microns in diameter, with an acoustic impedance at least 2 times different than that of blood plasma) between 0.5-8 MHz with a single acoustic pulse of 1-5 cycles, while simultaneously receiving echo signatures with frequencies content between 15-75 MHz.

In one embodiment, a dual frequency transducer is used to excite ultrasound contrast agents between 0.5-8 MHz and pulse lengths of 1-20 cycles, while simultaneously interrogating (transmit and receive) the contrast agents with a second pulse of 1-5 cycles at a high frequency, between 15-75 MHz.

In one embodiment, a dual frequency transducer is used to excite ultrasound contrast agents between 0.5-8 MHz and pulse lengths of 1-20,000,000 cycles in order to cause a physical translation of the contrast agent due to acoustic radiation force or acoustic streaming.

In one embodiment, a dual frequency transducer is used to excite ultrasound contrast agents between 0.5-8 MHz and pulse lengths of 1-20,000,000 cycles in order to cause a physical translation of the contrast agent due to acoustic radiation force or acoustic streaming, where the contrast agents are imaged within 5 seconds prior to and after the acoustic radiation force pulse. (imaging could be as described in 2, or 3, or with transmit and receive at frequencies from 15-75 MHz).

In one embodiment, a dual frequency transducer is used to excite ultrasound contrast agents between 0.5-8 MHz and pulse lengths of 1-20,000,000 cycles in order to cause a physical translation of the contrast agent due to acoustic radiation force or acoustic streaming, where the contrast agents are imaged during the acoustic radiation force pulse. (imaging could be as described in 2, or 3, or with transmit and receive at frequencies from 15-75 MHz).

In one embodiment, a dual frequency transducer is used to disrupt ultrasound contrast agents with acoustic pulses between 0.5-8 MHz, with simultaneous imaging at frequencies from 15-75 MHz The systems and methods described herein are not limited to use with ultrasound contrast agents, but may be used with drug-carrying microbubbles, microparticles, or acoustically active vehicles that carry a therapeutic agent, or with acoustically active vehicles that carry a gene delivery agent are utilized. For example, in one embodiment, a dual frequency transducer may be used to disrupt drug-carrying microbubbles, microparticles, or acoustically active vehicles that carry a therapeutic agent with acoustic pulses between 0.5-8 MHz, with simultaneous imaging at frequencies from 15-75 MHz, or to disrupt gene delivery vehicles with acoustic pulses between 0.5-8 MHz, with simultaneous imaging at frequencies from 15-75 MHz.

The systems and methods described herein may include or make use of software that allows selection of a region of interest, either in 2-D or 3-D, in combination with a dual-frequency transducer, where the overall image is created by the high-frequency component (15-75 MHz) of the transducer, and the low-frequency component of the transducer is energized selectively across only the region of interest. In one embodiment, a low frequency component, such as in the 0.5-8 MHz range, is used to apply acoustic radiation force in the selected area. Alternatively, the low frequency component may be used to fragment (disrupt) ultrasound contrast agents in the selected area or to fragment drug or gene delivery vehicles in the selected area. In one embodiment, a low frequency component, such as in the 0.5-5 MHz range, may be used cause local enhancement in vascular and/or cellular permeability with simultaneous imaging at 15-75 MHz. The systems and methods described herein may also be used in conjunction with administration of a microbubble or other cavitation nuclei.

Examples of the use of radiation force to direct carriers to a target site, fragment the carriers, and thus release therapeutic compounds, as well as targeting and fragmentation combined with imaging of the treatment site using HFUS frequencies less than or equal to 20 MHz, is described in U.S. Pat. No. 7,358,226, herein incorporated by reference in its entirety.

What is claimed is:

1. A method for high-frequency contrast imaging and image-guided therapeutics, the method comprising:
   generating and directing ultrasound energy with a transmitter of a first frequency bandwidth toward the volume to be imaged, the volume containing a carrier having non-linear acoustical properties, wherein the ultrasound energy of the first frequency bandwidth causes the carrier to generate ultrasound energy of a second frequency bandwidth that is different from the first frequency bandwidth, wherein the transmitter comprises a first physical component of a multi-frequency ultrasound transducer that is structured to transmit the ultrasound energy of the first frequency bandwidth and wherein the first frequency bandwidth has a center frequency in a range between 0.8 MHz and 10 MHz;
   detecting, from the volume to be imaged, the ultrasound energy with a receiver of a second frequency bandwidth, wherein the receiver comprises a second physical component of the multi-frequency ultrasound transducer structured to detect ultrasound energy at frequencies greater than 20 MHz wherein the first frequency bandwidth generated by the transmitter is lower than the second frequency bandwidth detected by the receiver and wherein the first and second physical components of the multi-frequency transducer are structured so that the −12 dB bandwidths of the transmitter and the receiver do not overlap with each other; and
   using the detected ultrasound energy of the second frequency bandwidth to generate an image of the volume to be imaged,
   wherein components of the second frequency bandwidth that are detected and used to generate the image are greater than 20 MHz.

2. The method of claim 1 wherein the components of the second frequency bandwidth that are detected are of a frequency greater than 25 MHz.

3. The method of claim 1 wherein the carrier comprises one of:
   an acoustically active liposphere;
   a liposome;
   a gas-filled agent; and
   a liquid perfluorocarbon droplet.

4. The method of claim 1 wherein the carrier comprises a contrast agent.

5. The method of claim 1 wherein the carrier comprises a substance having an acoustical property that is different from an acoustical property of biological tissue.

6. The method of claim 5 wherein the acoustical property that is different from an acoustical property of biological tissue comprises acoustic impedance.

7. The method of claim 1 wherein the carrier comprises a therapeutic compound.

8. The method of claim 1 wherein the carrier comprises an outer surface having at least one molecular structure for attaching the carrier to biological structures.

9. The method of claim 1 wherein the carrier comprises an outer surface having at least one molecular structure targeting a cell receptor.

10. The method of claim 1 wherein the ultrasound energy of the first frequency bandwidth is used for at least one of:
    affecting a position of the carrier;
    affecting a size of the carrier;
    affecting a structural integrity of the carrier;
    affecting the proximity of the carrier relative to a target portion of the volume to be imaged;
    affecting vascular permeability of tissue in the volume to be imaged;
    affecting the temperature within the volume to be imaged; and
    sonophoresis.

11. The method of claim 1 wherein the volume to be imaged includes at least one of a vein, an artery, a venule, an arteriole, a capillary, and a lymphatic.

12. A system for high-frequency contrast imaging and image-guided therapeutics, the system comprising:
    a multi-frequency ultrasound transducer including a transmitter comprising a first physical component structured to generate and transmit ultrasound energy at a first frequency bandwidth has a center frequency in a range between 0.8 MHz and 10 MHz and a receiver comprising a second physical component structured to detect ultrasound at a second frequency bandwidth different from the first frequency bandwidth, the second frequency bandwidth comprising frequencies greater than 20 MHz wherein the first frequency bandwidth generated by the transmitter is lower than the second frequency bandwidth detected by the receiver and wherein first and second physical components are structured such that −12 dB bandwidths of the transmitter and the receiver do not overlap with each other; and
    a control module for controlling the transmitter of the ultrasound transducer to generate and direct the ultrasound energy of the first frequency bandwidth, toward a volume to be imaged, the volume containing a carrier having non-linear acoustical properties, for causing the carrier to generate the ultrasound energy of the second frequency bandwidth, and for controlling the receiver of the ultrasound to detect, from the volume to be imaged, the ultrasound energy of the second frequency bandwidth; and for using the detected ultrasound energy of the second frequency bandwidth to generate an image of the volume to be imaged,
    wherein components of the second frequency bandwidth that are detected and used to generate the image are greater than 20 MHz.

13. The system of claim 12 wherein the components of the second frequency bandwidth that are detected are of a frequency greater than 25 MHz.

14. The system of claim 12 wherein the transducer transmits ultrasound energy at both the first and second frequency bandwidths simultaneously.

15. The system of claim 12 wherein the carrier comprises one of:

an acoustically active liposphere;
a liposome;
a gas-filled agent; and
a liquid perfluorocarbon droplet.

16. The system of claim 12 wherein the carrier comprises a contrast agent.

17. The system of claim 12 wherein the carrier comprises a substance having an acoustical property that is different from an acoustical property of biological tissue.

18. The system of claim 17 wherein the acoustical property that is different from an acoustical property of biological tissue comprises acoustic impedance.

19. The system of claim 12 wherein the carrier comprises a therapeutic compound.

20. The system of claim 12 wherein the carrier comprises an outer surface having at least one molecular structure for attaching the carrier to biological structures.

21. The system of claim 12 wherein the carrier comprises an outer surface having at least one molecular structure targeting a cell receptor.

22. The system of claim 12 wherein the ultrasound energy of the first frequency bandwidth is used for at least one of:
   affecting a position of the carrier;
   affecting a size of the carrier;
   affecting a structural integrity of the carrier;
   affecting the proximity of the carrier relative to a target portion of the targeted area;
   affecting vascular permeability of tissue in the targeted area;
   affecting temperature of a target portion of the targeted area; and
   sonophoresis.

23. The system of claim 12 wherein the targeted volume includes at least one of a vein, an artery, a venule, an arteriole, a capillary, and a lymphatic.

24. A non-transitory computer readable medium having stored thereon executable instructions that when executed by the processor of a computer control the computer to perform steps comprising:
   generating and directing ultrasound energy with a transmitter of a first frequency bandwidth toward the volume to be imaged, the volume containing a carrier having non-linear acoustical properties, wherein the ultrasound energy of the first frequency bandwidth causes the carrier to generate ultrasound energy of a second frequency bandwidth that is different from the first frequency bandwidth, wherein the transmitter comprises a first physical component of a multi-frequency ultrasound transducer that is structured to transmit the ultrasound energy of the first frequency bandwidth and wherein the first frequency bandwidth has a center frequency in a range between 0.8 and 10 MHz;
   detecting, from the volume to be imaged, the ultrasound energy with a receiver of a second frequency bandwidth, wherein the receiver comprises a second physical component of the multi-frequency ultrasound transducer structured to detect ultrasound energy at frequencies greater than 20 MHz wherein the first frequency bandwidth generated by the transmitter is lower than the second frequency bandwidth detected by the receiver and wherein the first and second physical components of the multi-frequency transducer are structured so that the −12 dB bandwidths of the transmitter and the receiver do not overlap with each other; and
   using the detected ultrasound energy of the second frequency bandwidth to generate an image of the volume to be imaged,
   wherein components of the second frequency bandwidth that are detected and used to generate the image are greater than 20 MHz.

* * * * *

UNITED STATES PATENT AND TRADEMARK OFFICE
CERTIFICATE OF CORRECTION

PATENT NO. : 9,532,769 B2
APPLICATION NO. : 13/393500
DATED : January 3, 2017
INVENTOR(S) : Dayton et al.

Page 1 of 1

It is certified that error appears in the above-identified patent and that said Letters Patent is hereby corrected as shown below:

In the Specification

Column 1, Lines 15-19:
Replace: "This presently disclosed subject matter was made with U.S. Government support under Grant No. 1R01EB009066-01 awarded by the National Institutes of Health. Thus, the U.S. Government has certain rights in the presently disclosed subject matter."
With: "This invention was made with government support under Grant Number EB009066 awarded by the National Institutes of Health. The government has certain rights in the invention."

Signed and Sealed this
Tenth Day of April, 2018

Andrei Iancu
*Director of the United States Patent and Trademark Office*